United States Patent [19]
Naoi et al.

[11] Patent Number: 5,579,783
[45] Date of Patent: Dec. 3, 1996

[54] O-RING TEST METHOD AND APPARATUS FOR MEASURING MUSCULAR STRENGTH

[75] Inventors: Takayoshi Naoi, Tokyo; Yoichiro Sako, Chiba; Minoru Ohzeki, Kanagawa; Tomoko Ono, Kanagawa; Mitsuyoshi Yamamoto, Kanagawa, all of Japan

[73] Assignee: Sony Corporation, Japan

[21] Appl. No.: 294,945

[22] Filed: Aug. 24, 1994

[30] Foreign Application Priority Data

Aug. 28, 1993 [JP] Japan ................................. 5-235503
Aug. 28, 1993 [JP] Japan ................................. 5-235504

[51] Int. Cl.$^6$ ................................. A61B 5/103
[52] U.S. Cl. ................................. 128/782
[58] Field of Search ................................. 128/774, 782; 33/511, 512

[56] References Cited

U.S. PATENT DOCUMENTS

| | | | |
|---|---|---|---|
| 4,846,462 | 7/1989 | Regnier et al. | 128/782 |
| 5,157,970 | 10/1992 | Lewis | 128/774 |
| 5,174,154 | 12/1992 | Edwards | 128/774 |
| 5,188,107 | 2/1993 | Omura | 128/630 |

*Primary Examiner*—Max Hindenburg
*Attorney, Agent, or Firm*—Ronald P. Kananen

[57] ABSTRACT

In a voluntary-muscle strength measurement method and a muscular tonus state judgment method, the muscle strength of a voluntary muscle and the muscular tonus state can be measured accurately and objectively. The muscle strength of a voluntary muscle as the examiner pulls apart an O-ring shape formed with the thumb and another finger of subject's hand is measured with a first sensor placed at at least one point on the two fingers forming O-ring shape, and it is detected whether or not two fingers forming O-ring shape were pulled apart with a second sensor placed between two fingers forming O-ring shape, and the muscle strength at the time two fingers forming O-ring shape were pulled apart is measured by the detected outputs of the first and second sensors. Thereby, the O-ring test can be executed accurately and the muscle strength of a voluntary muscle can be measured with high reliability. The pressure is applied to an O-ring shape formed with the thumb and another finger of subject's hand from outside through a pressure sensor by a pressure applying unit, and the applied pressure is measured from the output of the pressure sensor. The muscle tonus state when the pressure is applied to the O-ring shape can be judged by the period of time in which the result of measurement is higher than the predetermined value.

8 Claims, 26 Drawing Sheets

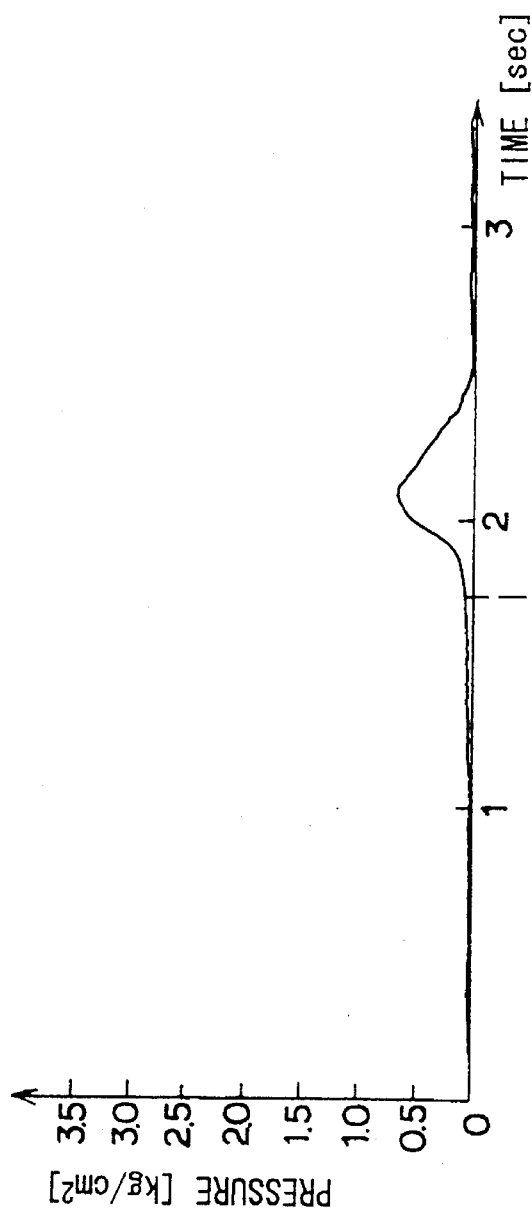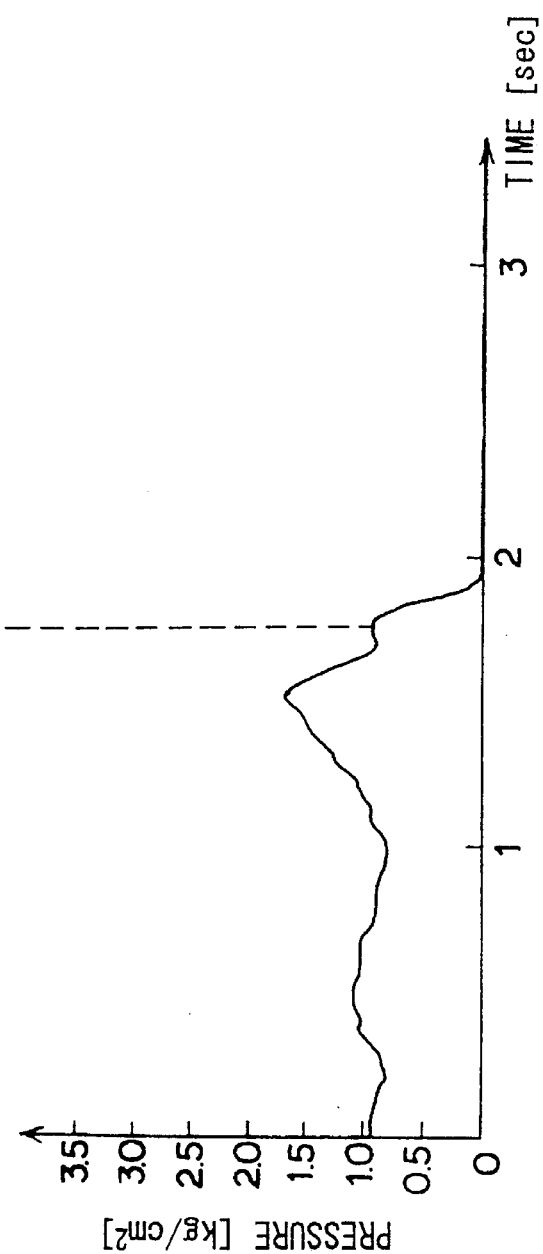
FIG. 11A
FIG. 11B

O-RING TEST METHOD AND APPARATUS FOR MEASURING MUSCULAR STRENGTH

BACKGROUND OF THE INVENTION

1. Field of the Invention

The present invention relates to a voluntary-muscle strength measurement method, a muscular tonus state judgment method, a voluntary-muscle strength measurement apparatus, a muscular tonus state judgment apparatus, a body-compatibility judgment method, abnormal area judgment methods, and information identification methods, and more particularly is applicable to the measurement of the muscle strength of the voluntary muscle and the judgment of the muscular tonus state as the examiner pulls apart an O-ring shape formed with the thumb and one of the fingers of the hand of a subject.

2. Detailed Description of the Related Art

It is known among medical diagnostic techniques to employ a bi-digital O-ring test, hereinafter referred to as "an O-ring test", to diagnose an abnormal area of a subject who is a patient, see, for example, U.S. Pat. No. 5,188,107. In the O-ring test, the subject forms an O-ring shape with one hand by placing the tip of the thumb against the tip of one of the fingers and forces the fingers together. The examiner attempts to pull apart the O-ring shape by pulling from both sides. The strength of the fingers of the subject opposing the examiner is then determined.

More particularly, the O-ring test is an in vivo sensor test making use of the muscular tonus state. If an arbitrary organ representation point is pointed to and the muscle strength of the fingers becomes weakened, the O-ring shape comes open. This means that the organ is abnormal. Conversely, when the O-ring shape cannot be pulled apart, the organ is normal. However, the meaning of the above is reversed in the case of the thymus gland. Thus, the abnormal areas of the body can be detected with this test.

In addition, if the same technique is performed by having a sample of a particular substance in the subject's hand, the muscle strength of the fingers of the subject will become weakened and the O-ring shape will be pulled apart if the same substance in subject's hand exists inside the body of the subject. This has been interpreted to be a phenomenon resulting from the resonance of the substances, and is therefore called a resonance test. Making use of this method, the internal distribution of bacteria, viruses, cancer, metabolic substances, hormones, nerve transmission substances, heavy metals, drugs, and the like in the human body can be determined and, in this way, diseases can be diagnosed. It is to be noted that the O-ring test is an auxiliary diagnostic method that is performed previous to the diagnosis made by using the latest regular medical equipment.

It can thus be actually detected, in the diagnosis of a subject, what type of abnormality exists and in which organ, by performing the O-ring test. At first, from the aspect of a diagnosis, assistance can be provided in the discovery of abnormal internal organs and imaging to the body surface; the determination of the cause of abnormal areas; the discovery and localization of diagnosis of bacteria, viruses, and first-stage cancers; the imaging and the change with the passage of time of metabolic substances, hormones and nerve transmission substances; and the auxiliary diagnosis of the cause of miscellaneous diseases, particularly those of an electromagnetic wave or the deposition of heavy metals.

Secondly, the O-ring test can also be used to determine the method of medical treatment. From the aspect of medical treatment, the O-ring test provides the determination of an effective drug and the determination of the optimum dosage, the judgment of the internal distribution of a substance in the body and the change with the passage of time and the adverse reaction to a medicinal substance, and the judgment of the effect of a medicine and the adverse reaction resulting from the use of multiple drugs. Thus, the O-ring test can be applied as a useful guide to diagnosis and medical treatment. Practically speaking, the O-ring test is applied to the judgment of the compatibility of various medicinal substances to the human body, the judgment of the abnormal area of a body, and the judgment of whether an arbitrary object and a particular object have the same information.

However, the O-ring test is conducted by using the fingers of the hand which is the voluntary muscle controlled at will by a person, so that there is a possibility that indeterminate factors may appear. For example, the cases may occur in which the subject forming the O-ring shape with two fingers and the examiner attempting to pull the O-ring shape apart participate in the O-ring test by using different finger strengths due to the difference in their respective wills. In addition, the voluntary muscle tends to be fatigued easily and, in some cases, the muscle strength of the voluntary muscle may be increased or decreased consciously. Therefore, the cases may occur in which the O-ring test cannot be performed accurately and objectively.

Further, in the O-ring test, the strength is represented as a number from +4 to −4, but this is no more than qualitative. In order to solve this problem, a peak value of the muscle strength can be detected by means of motor-driven equipment instead of the subject. However, the problem arises that the peak value itself changes and is not stable when a force is exerted only for a very short period of time, and that a competitive state of force is difficult to be made because a machine pulls at a constant speed and the finger is easily fatigued. Moreover, a dynamometer, a pinch meter, and the like can be used to meter a pushing force, not a pulling force, but the problem arises that their reproducibility is poor as the O-ring test and the fatigue of the finger is fast.

SUMMARY OF THE INVENTION

In view of the foregoing, a first object of this invention is to provide a voluntary-muscle strength measurement method and apparatus thereof, a body-compatibility judgment method, an abnormal area judgment method, and an information identification method, in which it is possible to conduct the O-ring test accurately and objectively, to measure the muscle strength of the voluntary muscle with high reliability, to judge and identify information on the compatibility and the abnormal area of the human body.

A second object of the invention is to provide a muscular tonus state judgment apparatus and method thereof, a body-compatibility judgment method, an abnormal area judgment method, and an information identification method, in which it is possible to conduct the O-ring test accurately and objectively, to judge the muscular tonus state with high reliability, and to judge and identify information on the compatibility and the abnormal area of the human body.

The first object and other objects of the invention have been achieved by the provision of the voluntary-muscle strength measurement method for measuring the muscle strength of the voluntary muscle as an examiner pulls apart the O-ring shape 6 formed with the thumb and another finger of the hand of a subject. In the voluntary-muscle strength measurement method, the muscle strength involved as the examiner pulls apart the O-ring shape is detected with a first sensor 2 placed on at least one point on the thumb or the finger of the hand of the subject. It is detected whether the thumb and the finger of the hand of the subject are pulled apart by using a second sensor 3 placed between the thumb and the finger of the hand of the subject. The muscle strength at the time the thumb and the finger of the hand of the subject are pulled apart is then measured by the measured outputs of the first and second sensors 2 and 3.

According to the present invention, there is also provided a voluntary-muscle strength measurement apparatus 1 for measuring the muscle strength of the voluntary muscle as the examiner apart the O-ring shape 6 formed when the tip of the thumb of the hand of a subject is made to touch the tip of one of the fingers on the same hand of a subject. The apparatus comprises a firs sensor 2 which detects the muscle strength as the examiner pulls apart the O-ring shape and which is placed on at least one point on the thumb or the finger of the hand of the subject. A second sensor 3 detects whether the thumb and the finger of the hand of the subject are pulled apart and is placed between the thumb and the finger of the hand of the subject. The muscle strength at the time that the thumb and the finger of the hand of the subject are pulled apart is measured by the detected outputs of the first and second sensors 2 and 3.

According to the present invention, there is also provided a body-compatibility judgment method RTO for judging the compatibility of the human body in utilizing the voluntary-muscle strength measurement apparatus 1, comprising the steps of measuring the muscle strength at the time that the thumb and the finger of the hand of the subject are pulled apart in a normal state (SP1), measuring the muscle strength at the time that the thumb and the finger of the hand of the subject are pulled apart in a state in which a particular object 30 is indicated is also measured (SP2), and comparing the measured muscle strengths and judging if the particular object 30 is compatible with the subject (SP3).

According to the present invention, there is also provided an abnormal area judgment method RT10 for judging an abnormal area of the human body in utilizing the voluntary-muscle strength measurement apparatus 1, comprising the steps of detecting the muscle strength at the time that the thumb and the finger of the hand of the subject are pulled apart in a normal state (SP11), measuring the muscle strength at the time that the thumb and the finger of the hand of the subject are pulled apart in a state in which a particular part of the body is indicated (SP12), and comparing the measured muscle strengths and judging if the particular part of the body is abnormal (SP13).

According to the present invention, there is also provided an information identification method RT20 for identifying information by the use of the voluntary-muscle strength measurement apparatus 1. The method comprises the steps of detecting the muscle strength at the time that the thumb and the finger of the hand of the subject are pulled apart in a state in which a particular object 50 is contacted (SP21), detecting the muscle strength at the time that the thumb and the finger of the hand of the subject are pulled apart in a state in which a particular object 50 is contacted and arbitrary objects 52 to 54 are indicated (SP22), and comparing the detected muscle strengths and judging if the arbitrary objects 52 to 54 and the particular object 50 have the same information (SP23).

The second object and other objects of the invention have been achieved by the provision of a muscular tonus state judgment method comprising the steps of applying a pressure W from the outside through a pressure sensor 16 to an O-ring shape 19 formed with the thumb and one of the fingers of the hand of a subject by a pressure applicator 15. The pressure applied to the O-ring shape 19 from the output of the pressure sensor 16, and judging the muscular tonus state as pressure W is applied to the O-ring shape 19 for a period of time in which the measured pressure is more than a predetermined value WT.

According to the present invention, there is also provided a muscular tonus state judgment apparatus comprising a pressure applicator means 15 for applying pressure W from the outside through the pressure sensor 16 to the O-ring shape 19 formed with the thumb and one of fingers of the hand of a subject. A sensing device measures the pressure W applied to the O-ring 19 from the output of the pressure sensor 16 and measures a period of time in which the measured pressure is more than a predetermined value WT. The muscular tonus state as the pressure W is applied to the O-ring shape 19 is judged according to the period of time.

According to the present invention, there is also provided a body-compatibility judgment method for judging the compatibility of the human body by the use of the muscular tonus state judgment apparatus. Pressure W is applied from the outside through the pressure sensor 16 to the O-ring shape 19 formed with the thumb and one of the fingers of the hand of a subject, and simultaneously the subject contacts a particular object. The pressure W that is applied to the O-ring shape 19 is measured from the output of the pressure sensor 16. When the period of time, showing that the measured result is more than a predetermined value WT, is more than a first threshold value TH2, it is judged that the particular object 60 is compatible with the body of the subject. When the period of time is less than a second threshold value TH1, it is judged that the particular object 60 is not compatible with the body of the subject.

According to the present invention, there is also provided an abnormal area judgment method for judging an abnormal area of the human body by the use of the muscular tonus state judgment apparatus 20. Pressure W is applied from the outside through the pressure sensor 16 to the O-ring shape 19 formed with the thumb and one of the fingers of the hand of a subject, and simultaneously the subject indicates a predetermined part of the body. The pressure W applied to the O-ring shape 19 is measured from the output of the pressure sensor 16 and when the period of time, showing that the measured pressure is more than a predetermined value WT, is less than a second threshold value TH1, it is judged that the predetermined area is abnormal.

According to the present invention, there is also provided an information identification method for identifying information by the use of the muscular tonus state judgment apparatus 20. Pressure W is applied from the outside through the pressure sensor 16 to the O-ring shape 19 formed with the thumb and one of the fingers of the hand of a subject, and simultaneously. The subject contacts a particular object 80. The subject indicates an arbitrary object 82 to 84. The pressure W applied to the O-ring shape 19 is measured from the output of the pressure sensor 16. When the period of time, showing that the measured pressure is more than a predetermined value WT, is less than a second threshold value TH1, it is judged that the particular object 80 and the arbitrary object 82 to 84 have the same information.

In accordance with the achievement of the first object in this invention, the muscle strength as the examiner pulls apart the O-ring shape 6 is detected by a first sensor 2 placed on at at least one point on the thumb and the finger of the hand of the subject. It is also detected if the thumb and the finger of the hand of the subject are pulled apart with a second sensor 3 placed between the thumb and the finger of the hand of the subject. The muscle strength at the time that the thumb and the finger of the hand of the subject are pulled apart are then measured from the detected outputs of the first and second sensors 2 and 3. Accordingly, there can be provided voluntary-muscle strength measurement method and apparatus thereof which are capable of performing the O-ring test accurately and objectively and detecting the muscle strength of the voluntary muscle with high reliability.

In addition, with the aid of the voluntary-muscle strength measurement apparatus 1, the muscle strength is detected at the time that the thumb and the finger of the hand of the subject are pulled apart in a normal state. The muscle strength at the time that the thumb and the finger of the hand of the subject are pulled apart in a state that a particular object 30 is indicated is also measured. It is then judged if the particular object 30 is compatible with the subject by comparing the detected muscle strengths. Accordingly, there can be provided the body-compatibility judgment method which makes it possible to conduct the O-ring test accurately and objectively and makes it possible to judge the compatibility with the human body with high reliability.

Further, with the aid of the voluntary-muscle strength measurement apparatus 1, the muscle strength is detected at the time that the thumb and the finger of the hand of the subject are pulled apart in a normal state, and simultaneously the muscle strength at the time that the thumb and the finger of the hand of the subject are pulled apart in a state where a particular part of the body is indicated is also measured. The detected muscle strengths are compared to judge whether the particular part of the human body is abnormal. Accordingly, there can be provided the abnormal area judgment method which makes it possible to conduct the O-ring test accurately and objectively and makes it possible to judge an abnormal area of the body with high reliability.

Moreover, with the aid of the voluntary-muscle strength measurement apparatus 1, the muscle strength at the time that the thumb and the finger of the hand of the subject are pulled apart in a state where a particular object 50 is contacted is detected. Simultaneously, the muscle strength at the time that the thumb and the finger of the hand of the subject are pulled apart in a state where a particular object 50 is contacted and arbitrary objects 52 to 54 are indicated is also detected. The detected muscle strengths are compared to judge whether the arbitrary objects 52 to 54 and the particular object have the same information. Accordingly, there can be provided the information identification method which makes it possible to conduct the O-ring test accurately and objectively and makes it possible to identify information with high reliability.

In accordance with the achievement of the second object in this invention, with pressure applicator means 15, pressure W is applied from the outside through the pressure sensor 16 to the O-ring shape 19 formed with the thumb and one of the fingers of the hand of a subject. The pressure W applied to the O-ring shape 19 is measured from the output of the pressure sensor 16, and then the muscular tonus state as pressure W is applied to the O-ring shape 19 is detected from the period of time showing that the measured pressure is more than a predetermined value WT. Accordingly, there can be provided the muscular tonus state judgment method and apparatus thereof which make it possible to conduct the O-ring test accurately and objectively and make it possible to judge the muscular tonus state with high reliability.

In addition, in the body-compatibility judgment method for judging the compatibility of the human body by the use of the muscular tonus state judgment apparatus 20, pressure W is applied from the outside through the pressure sensor 16 to the O-ring shape 19 formed with the thumb and one of the fingers of the hand of a subject, and simultaneously the subject contacts a particular object 60. Then, pressure W applied to the O-ring shape 19 is measured from the output of the pressure sensor 16. It is judged that the particular object 60 is compatible with the body of the subject when the period of time, showing that the measured pressure is more than a predetermined value WT, is more than a first threshold value TH2. It is judged that the particular object 60 is not compatible with the body of the subject when the period of time is less than a second threshold value TH1. Accordingly, there can be provided a body-compatibility judgment method which makes it possible to judge the muscular tonus state accurately and objectively and to judge the compatibility of the human body with high reliability.

In addition, in the abnormal area judgment method for judging an abnormal area of the human body by the use of the muscular tonus state judgment apparatus 20, pressure W is applied from the outside through the pressure sensor 16 to the O-ring shape 19 formed with the thumb and one of the fingers of the hand of a subject, and simultaneously the subject indicates a predetermined part of the body. Then, pressure W applied to the O-ring shape 19 is measured from the output of the pressure sensor 16, and it is judged that the predetermined area is abnormal when the period of time, showing that the measured pressure is more than a predetermined value WT, is less than a second threshold value TH1. Accordingly, there can be provided the abnormal area judgment method which makes it possible to conduct the O-ring test by judging the muscular tonus state accurately and objectively and also makes it possible to judge an abnormal area of the human body with high reliability.

In addition, in the information identification method for identifying information by the use of the muscular tonus state judgment apparatus 20, pressure W is applied from the outside through the pressure sensor 16 to the O-ring shape 19 formed with the thumb and one of the fingers of the hand of a subject. Simultaneously, the subject contacts a particular object 80 and indicates an arbitrary object 82 to 84. The pressure W applied to the O-ring shape 19 is measured from the output of the pressure sensor 16, and it is judged that the particular object 80 and the arbitrary object 82 to 84 have the same information when the period of time showing that the measured pressure is more than a predetermined value WT is less than a second threshold value TH1. Accordingly, there can be provided the information identification method which makes it possible to judge the muscular tonus state accurately and objectively and also makes it possible to identify information with high reliability.

The nature, principle of utility of the invention will become more apparent from the following detailed description when read in conjunction with the accompanying drawings in which like parts are designated by like reference numerals or characters.

BRIEF DESCRIPTION OF THE DRAWINGS

In the accompanying drawings:

FIGS. 11A and 11B are characteristic curvilinear diagrams showing outputs obtained in a state where a card or which an arrow directed toward the inside of the human body is marked is placed, i.e., in the negative O-ring state, as an embodiment of the body-compatibility judgment method;

DETAILED DESCRIPTION OF THE EMBODIMENT

Figure 1:
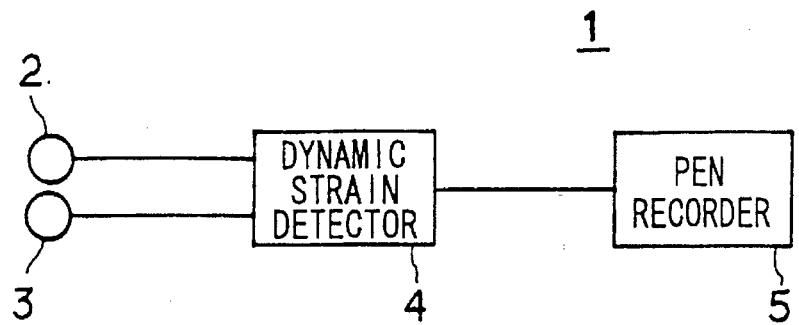
FIG. 1 is a block diagram showing the construction of a voluntary-muscle strength measurement apparatus according to an embodiment of the present invention.

Preferred embodiments of this invention will be described with reference to the accompanying drawings:

(1) First Embodiments (1-1) Voluntary-muscle strength measurement method of the embodiment In FIG. 1, 1 denotes a voluntary-muscle strength measurement apparatus in accordance with the present invention. The outputs of first and second pressure sensors 2 and 3 are inputted to a dynamic strain detector 4. The output of the dynamic strain detector 4 is inputted to a pen recorder 5, in which the changes in the pressures detected with the pressure sensors 2 and 3 are recorded on paper. In this embodiment, the pen recorder 5 has two channels so that the pressure change in the first pressure sensor 2 and the pressure change in the second pressure sensor 3 can be recorded simultaneously.

Figure 2:
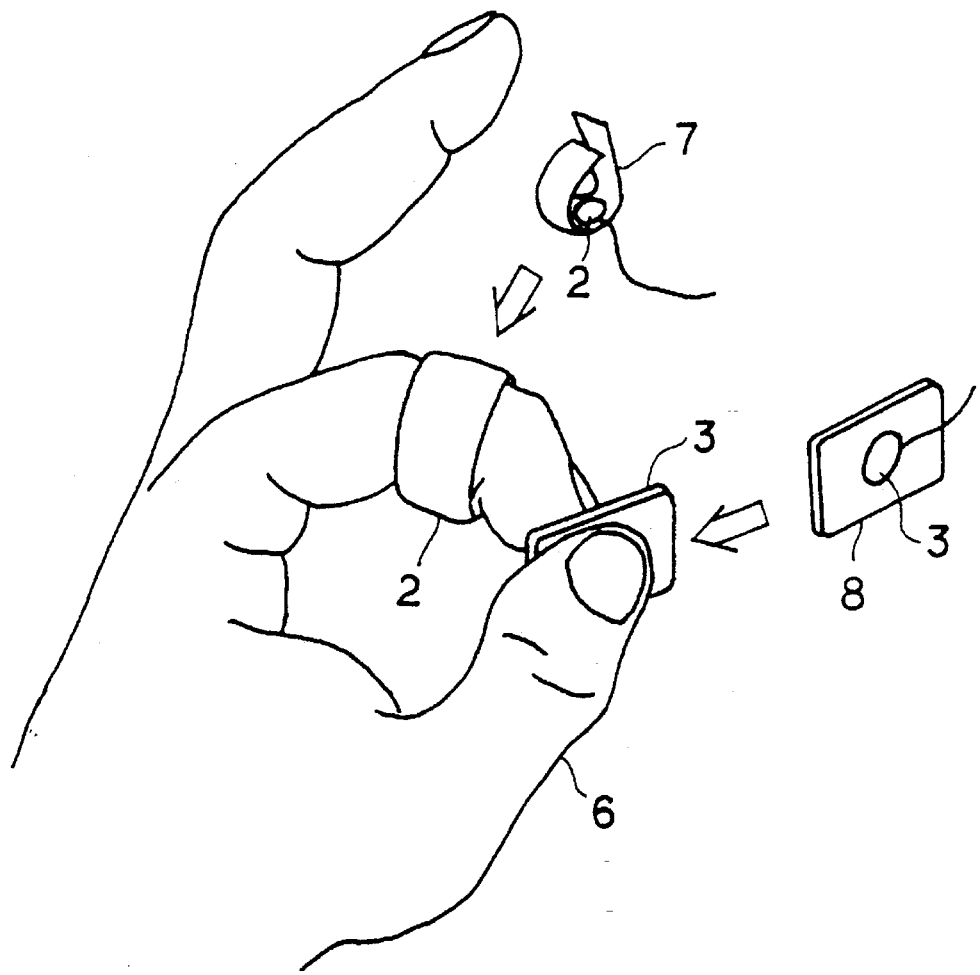
FIG. 2 is a schematic diagram showing the attachment of the pressure sensors of the voluntary-muscle strength measurement apparatus in FIG. 1.

Each of the pressure sensors 2 and 3 use a foil strain gauge in its transducing element, and are composed of a small and thin bridge pressure transducer. For example, the pressure sensors 2 and 3 are selected to have a thickness of about 0.6 mm and a diameter of about 6 mm. As shown in FIG. 2, the first pressure sensor 2 is placed in the vicinity of the second joint of the finger of the hand of a subject forming a part of an O-ring shape 6, while the second pressure sensor 3 is placed between the fingertips with which the O-ring shape 6 of the hand of a subject is formed. The first pressure sensor 2 is attached to surgical tape 7 so that the sensor 2 can be held in position easily, and the second pressure sensor 3 is attached to a sheet material 8.

Figure 3:
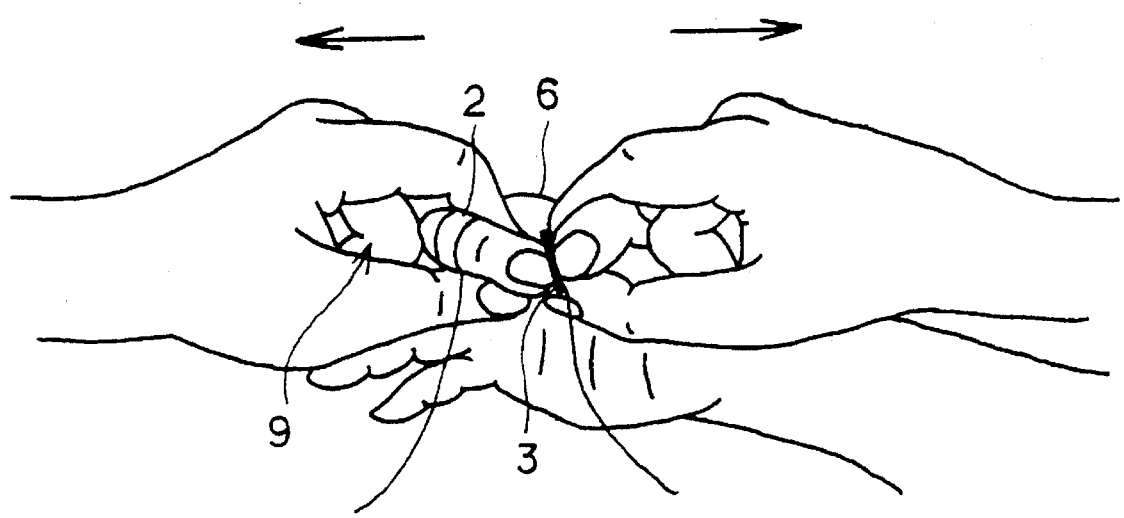
FIG. 3 is a schematic diagram explaining the O-ring ring test.

In the state where the pressure sensors 2 and 3 are held in position as shown in FIG. 2, the O-ring test is executed by putting the O-ring shape 9 of the hand of the examiner on the pressure sensor 2 and by pulling the O-ring shape 6 of the hand of the subject in the directions indicated the arrows with the O-ring shapes 9 of the hand of the examiner, as shown in FIG. 3. As a result, the finger strengths measured with the pressure sensors 2 and 3, i.e., changes in the muscle strength of the voluntary muscle are obtained as graphs g1 and g2 shown in FIGS. 4A and 4B. Practically, the graph g1 obtained by the pressure sensor 2 shows the pressure changes as the O-ring shape 6 of the hand of the subject is being pulled apart by the O-ring shapes 9 of the hands of the examiner, and the graph g2 obtained by the pressure sensor 3 shows the time when the fingertips in the O-ring shape 6 of hand of the subject were pulled apart.

In the O-ring test, the compatibility of the human body, an abnormal area, information identification, and the like are judged by the O-ring state of the subject as the test result. As the O-ring state, there are two kinds of states, one in which the O-ring shape cannot be pulled apart, and one in which the O-ring shape can be pulled apart, hereinafter referred to as "a negative O-ring state". Further, the state in which the O-ring shape cannot be pulled apart is divided into a state where the O-ring shape is closed with a stronger force than usual, hereinafter referred to as "a positive O-ring state", and a state where the O-ring shape is closed with a force equal to a force at a normal time, hereinafter referred to as "a controlled state".

Figure 4A:
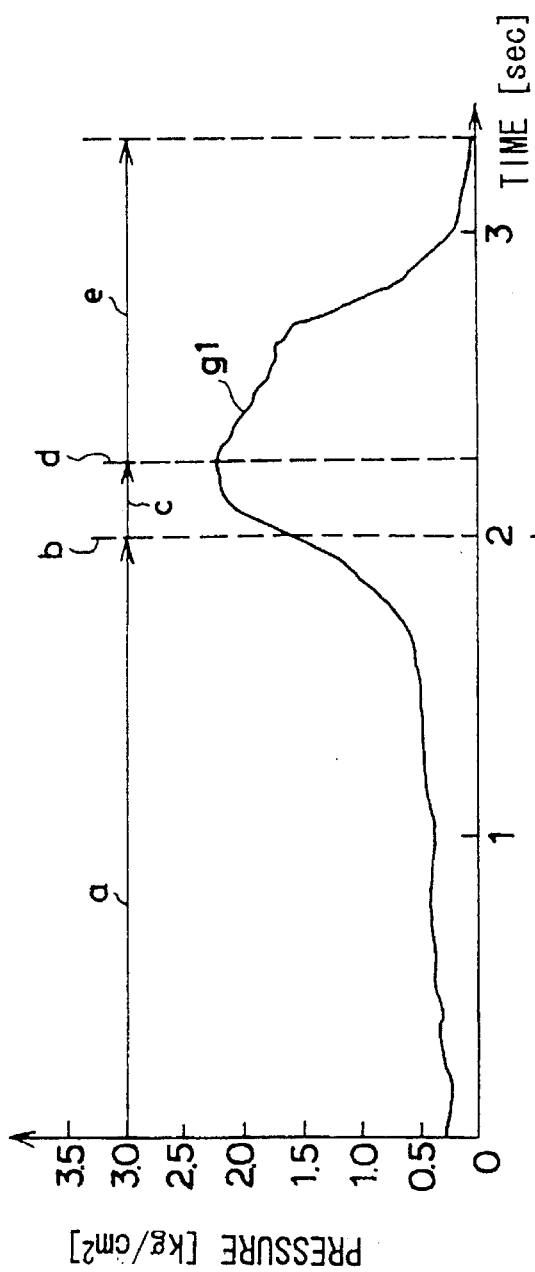
FIGS. 4A and 4B are characteristic curvilinear diagrams showing the outputs of the pressure sensors.
Figure 4B:
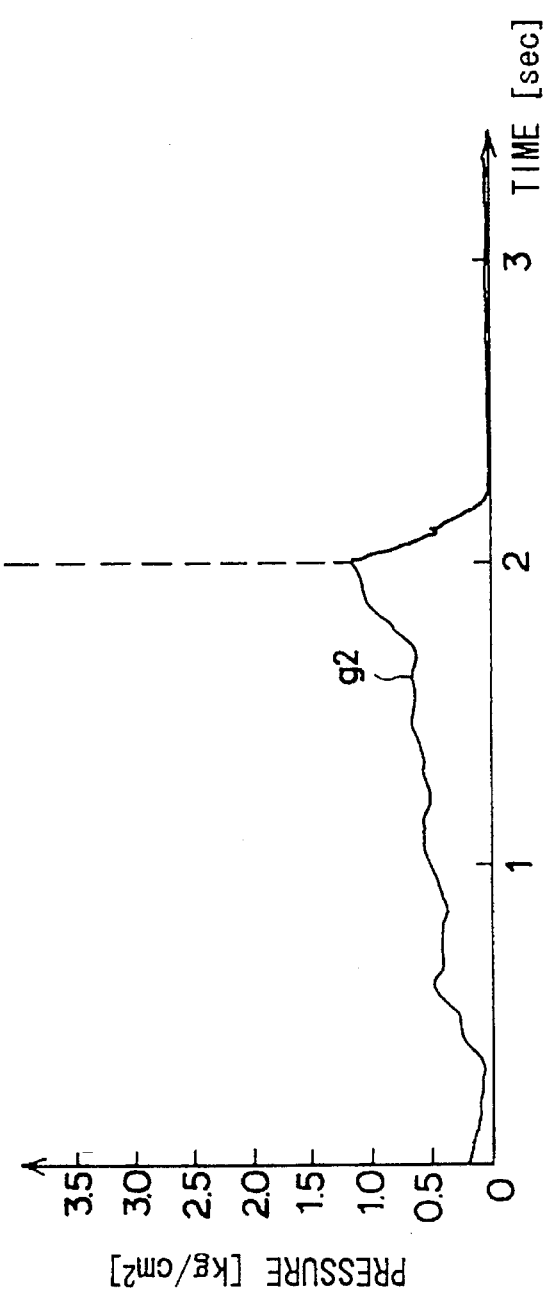

IF the voluntary-muscle strength measurement apparatus 1, the graphs g1 and g2 in FIGS. 4A and 4B are analyzed for five intervals, "a", "b", "c", "d", and "e". More particularly, the first interval "a" is an interval when the fingertips of the O-ring shape 6 of the hand of a subject are closed and the examiner begins the pulling apart of the O-ring shape 6 of the hand of the subject is started by the O-ring shapes 9 of the hands of the examiner. The second interval "b" is the moment when the fingertips of the O-ring shape 6 of the hand of the subject are pulled apart while the examiner continues to pull apart the O-ring shape 6 of the hand of the subject with the O-ring shapes 9. Further, the third to fifth intervals, "c", "d", and "e" are intervals in which the fingertips of the O-ring shape 6 of the hand of the subject are pulled apart. In the third interval "c", the examiner continues pulling apart the O-ring shape 6 of the hand of the subject; in the fourth interval "d", the examiner gives maximum pulling force; and, in the fifth interval "e", the examiner is about to finish pulling apart the O-ring shape 6 of the hand of the subject.

For such graphs g1 and g2, when the case of the controlled state and the case of the negative O-ring state are compared, the negative O-ring state has the following characteristics. When the pressure values "p" of the second interval "b" of the graph g1 in the controlled state and in the negative O-ring state are compared, the value in the negative O-ring state is smaller than that in the controlled state. Since the second interval "b" is the moment when the fingertips of the O-ring shape 6 of the subject are pulled apart, the pressure value "p" in the second interval "b" can be judged as the force necessary for pulling apart the fingertips of the O-ring shape 6 of the subject. From the fact that the pressure value in the negative O-ring state becomes smaller compared to that in the controlled state, it means that a reduction in the muscle strength of the O-ring shape 6 of the hand of the subject has occurred in the negative O-ring state.

Assuming that an area "s" is defined as an area surrounded by the X-axis, the pressure curve of the graph g1, and the straight lines extending from the interval "b" on the X-axis to the pressure curve. When the area "s" of the controlled state and the same area of the negative O-ring state are compared, the area "s" in the negative O-ring state is smaller than that in the controlled state. This area "s" represents an integration of forces from the time when a force is exerted on the O-ring shape 6 of the hand of the subject to the time when the fingertips of the O-ring shape 6 of the hand are pulled apart. If a reduction in the muscle strength of the subject occurs in the negative O-ring state, the area "s" becomes smaller because the fingertips are pulled apart earlier, assuming the pulling forces are the same.

Further, the falling gradient in the interval "e" is different for the case of the controlled state than for the case of the negative O-ring state. The falling gradient represents pressure changes occurring after the force exerted on the O-ring shape 6 of the hand of the subject has passed the maximum point. In the controlled state, the state that the finger strength of the subject competes with that of the examiner continues, and finally the force is removed in response to the will to complete the measurement of the examiner. As will be seen from the pressure curve, the pressure value in the vicinity of the maximum pressure continues for a while, and thereafter, the pressure is decreased. Thus, the controlled state is characterized by the fact that the pressure value in the vicinity of the maximum value continues flat. In contrast, in the case of the negative O-ring state, since the subject's fingers are pulled apart as soon as the maximum pressure is exerted, the pressure is decreased quickly after passing by the point of maximum pressure.

Figure 5A:
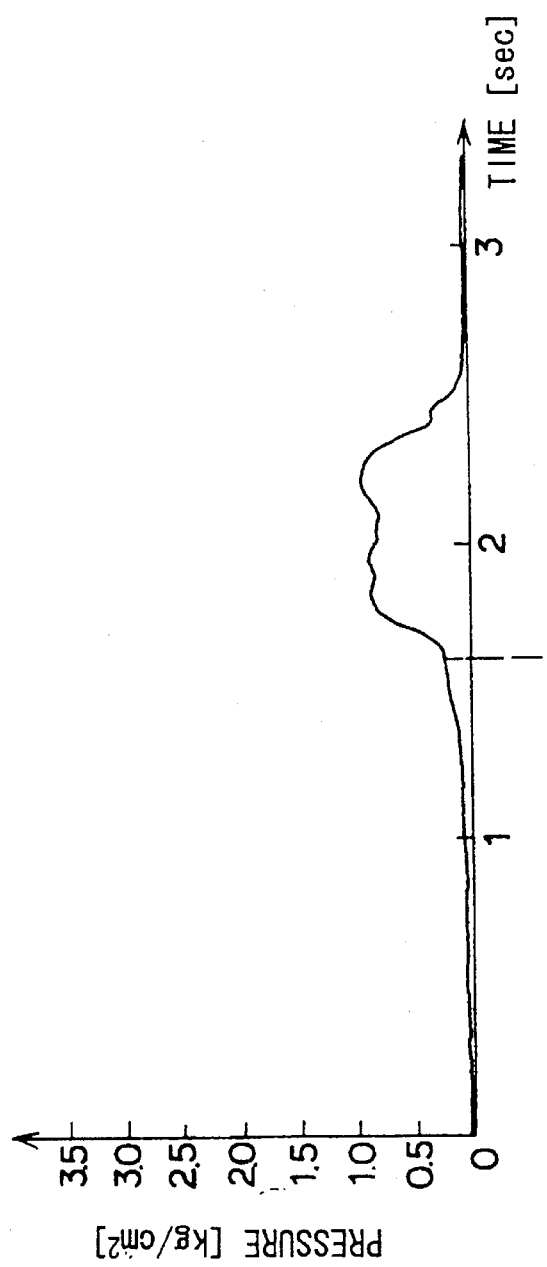
FIGS. 5A and 5B are characteristic curvilinear diagrams showing the outputs of the pressure sensors in a controlled state.
Figure 5B:
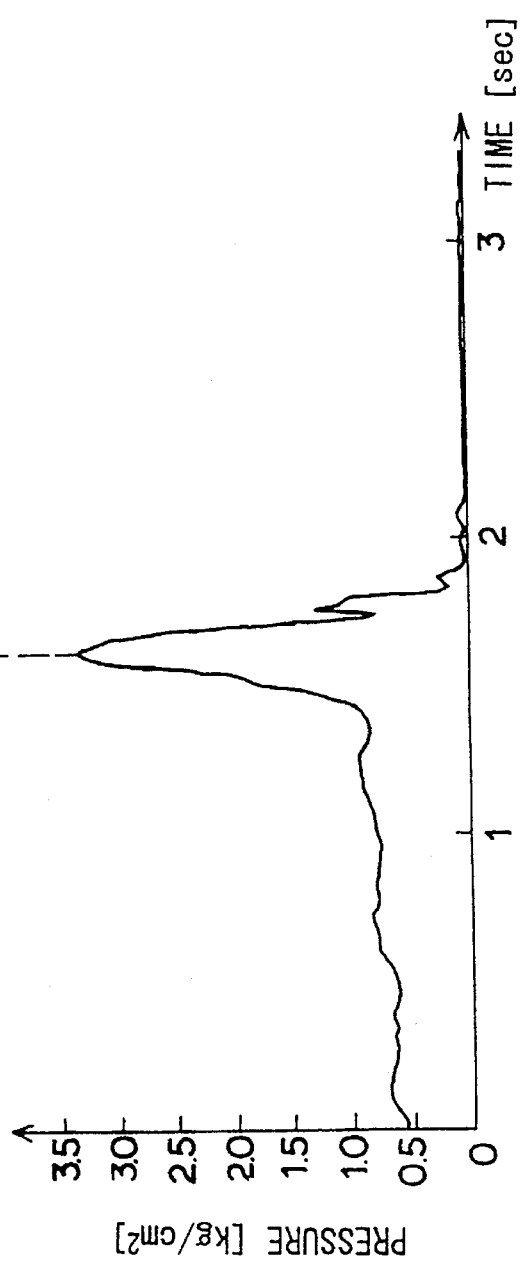
Figure 6A:
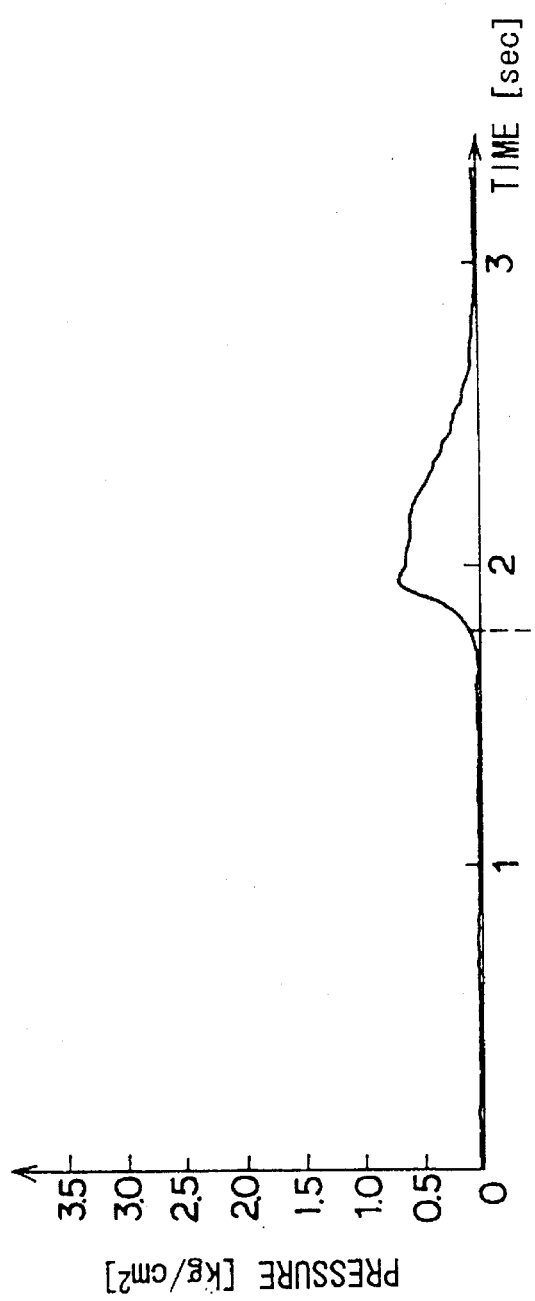
FIGS. 6A and 6B are characteristic curvilinear diagram is showing the outputs of the pressure sensors in a negative O-ring state.
Figure 6B:
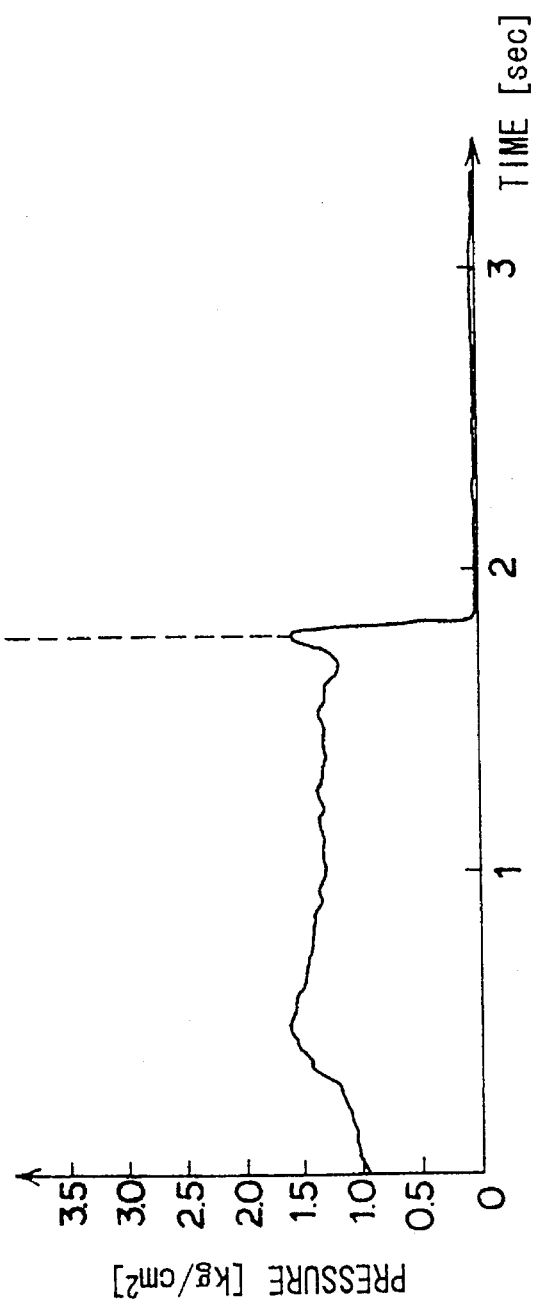

The measurement result when the controlled state is shown in FIGS. 5A and 5B, and the measurement result in the case of the negative O-ring state is shown in FIGS. 6A and 6B. FIGS. 5A, 5B, 6A and 6B show examples of the judgment of the compatibility of the human body in the form of the O-ring test. FIGS. 5A and 5B show the case where the subject grasps a life-root stone as a high bodycompatibility substance in one hand and executes the Oring test using the O-ring shape 6 formed with the fingers of the other hand, so that the controlled state is measured. FIGS. 6A and 6B show the case where the subject grasps arsenic as a low body-compatibility substance in one hand and executes the O-ring test using the O-ring shape 6 formed with the fingers of the other hand, so that and the negative O-ring state is measured.

From these figures, the pressure value "p" in the interval "b" is 200 $g/cm^2$ for the controlled state, and about 100 $g/cm^2$ for the negative O-ring state. It can also be understood that the area "s" in the controlled state is wider than the same in negative Oring state. It will further be understood that, for a difference in the gradient in the interval "e", the pressure value in the vicinity of the maximum value continues for a while in the case of the controlled state. On the other hand, in the case of the negative O-ring state, the pressure value is decreased after the maximum value.

According to the structure described above, when measuring the finger strength as the examiner pulls apart the O-ring shape 6 formed by the hand of the subject, the muscle strength as the examiner pulls apart the O-ring shape 6 of the hand of the subject is detected with the pressure sensor 2 placed on one point on the finger of the O-ring shape 6 of the subject. At the same time, it is determined whether the two fingers forming the O-ring shape are pulled apart with the pressure sensor 3 placed between the fingertips of the two fingers forming the O-ring shape. Since the muscle strength at the time that two fingers of the hand of the subject forming O-ring shape are pulled apart is measured with the detected outputs of the pressure sensors 2 and 3, the interference of external influences can be prevented. Therefore, it is possible to provide the voluntarymuscle strength measurement method and apparatus thereof in which make it possible to detect accurately and objectively the muscle strength of the voluntary muscle exerted in the O-ring test with high reliability.

(1-2) Body-compatibility judgment method by the voluntary-muscle strength measurement apparatus A body-compatibility judgment method for judging the compatibility of a particular object to a subject will hereinafter be described with the voluntary-muscle strength measurement apparatus 1 described above. In this embodiment, a telephone card, ginseng, a card on which an arrow directed toward a fingertip is marked, and a card on which an arrow directed toward the inside of the human body is marked are used as particular objects, and it is judged if these particular objects are compatible with the subject.

Figure 7:
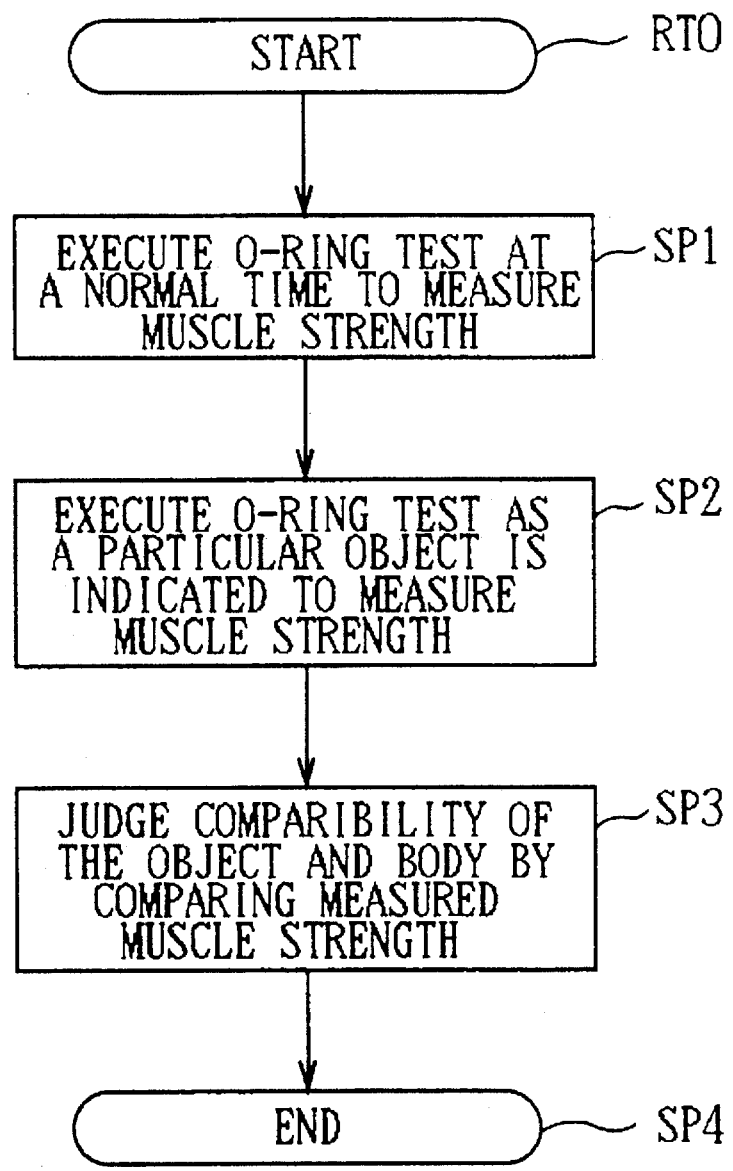
FIG. 7 is a flowchart showing a body-compatibility judgment procedure according to an embodiment of a body-compatibility judgment method of the present invention.
Figure 8A:
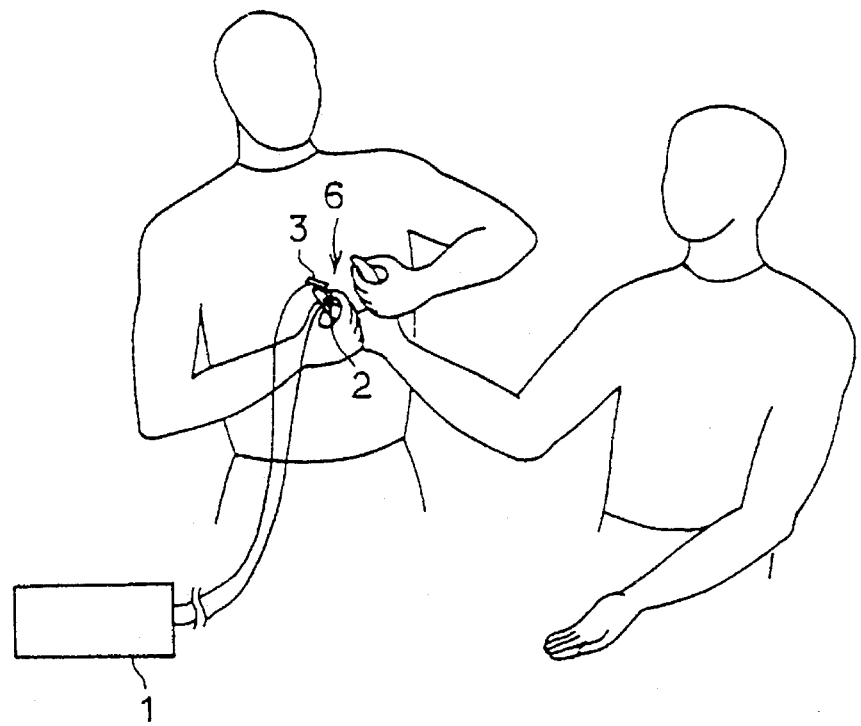
FIGS. 8A and 8B are schematic diagrams explaining the body-compatibility judgment method in FIG. 7.

The body-compatibility judgment method is executed with a body-compatibility judging procedure RTO shown in FIG. 7. At step SP1, the O-ring test is executed at a normal time and the muscle strength at that time is measured with the voluntary-muscle strength measurement apparatus 1. As shown in FIG. 8A, the normal time is set as a state that nothing is placed on the subject's left hand, and the muscle strengths obtained at that time with the pressure sensors 2 and 3 are measured in utilizing the voluntary-muscle strength measurement apparatus 1. As described with reference to FIG. 2, for the O-ring shape 6 formed with the subject's right hand, one pressure sensor 2 attached to surgical tape 7 is placed in the vicinity of the second joint of the finger and the other pressure sensor 3 is placed and held between the thumb and the finger.

Figure 8B:
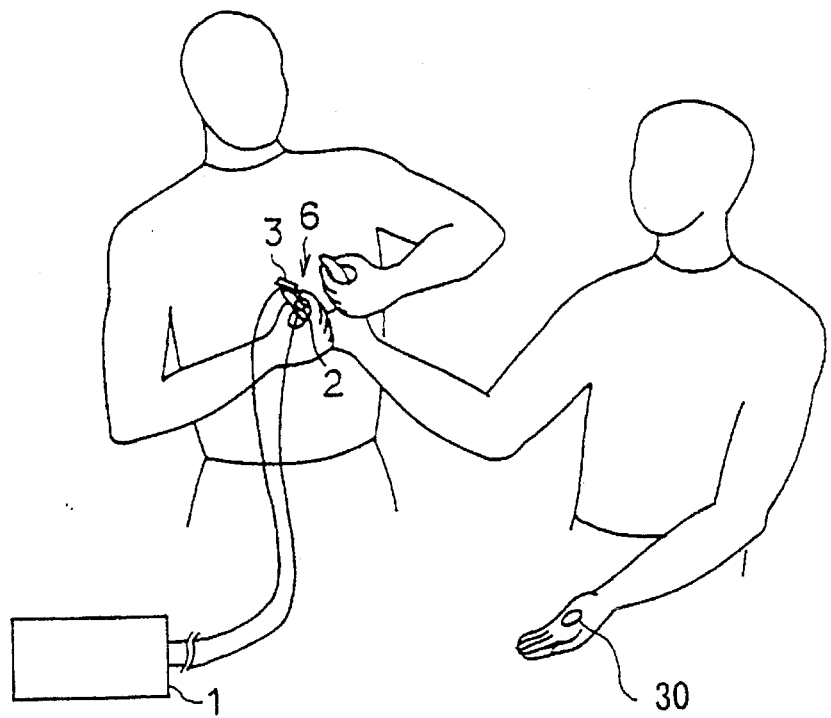

Next, at step SP2, the O-ring test is executed in a state where a particular object is indicated. As shown in FIG. 8B, the particular object 30, such as a telephone card, ginseng, a card on which an arrow directed toward a fingertip is marked, and a card on which an arrow directed toward the inside of the human body is marked, is placed on the subject's left hand, and the muscle strengths obtained with the pressure sensors 2 and 3 are measured in utilizing the voluntary-muscle strength measurement apparatus 1. At step SP3, it is judged if the particular object 30 is compatible with the subject, by comparing the muscle strengths measured in steps SP1 and SP2.

Figure 9A:
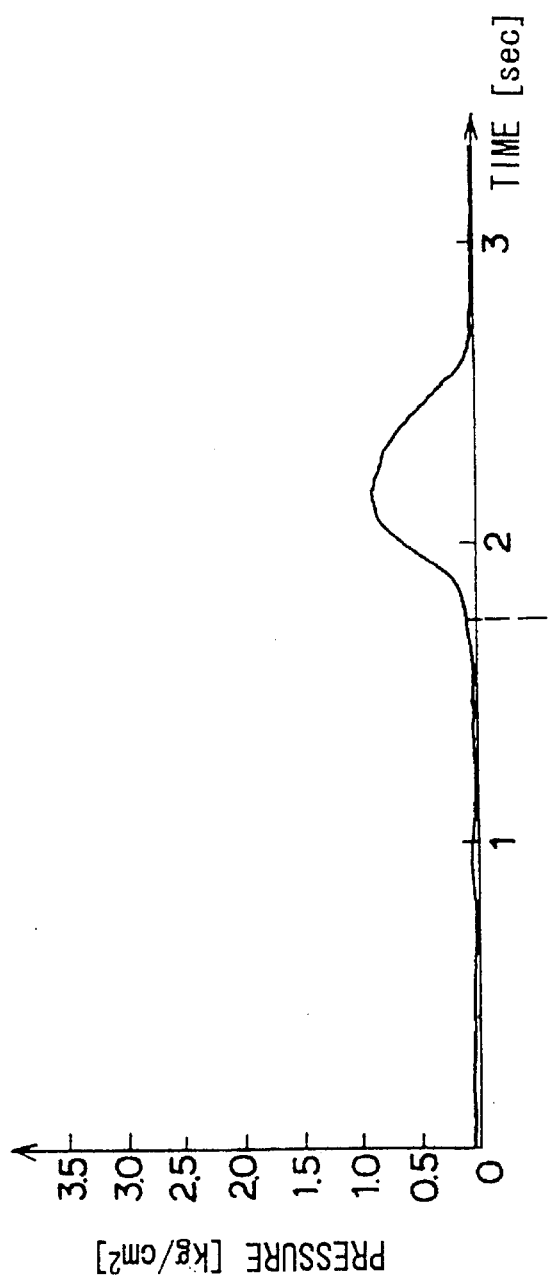
FIGS. 9A and 9B are characteristic curvilinear diagrams showing outputs obtained in a normal state, i.e., in a controlled state, as an embodiment of the body-compatibility judgment method.
Figure 9B:
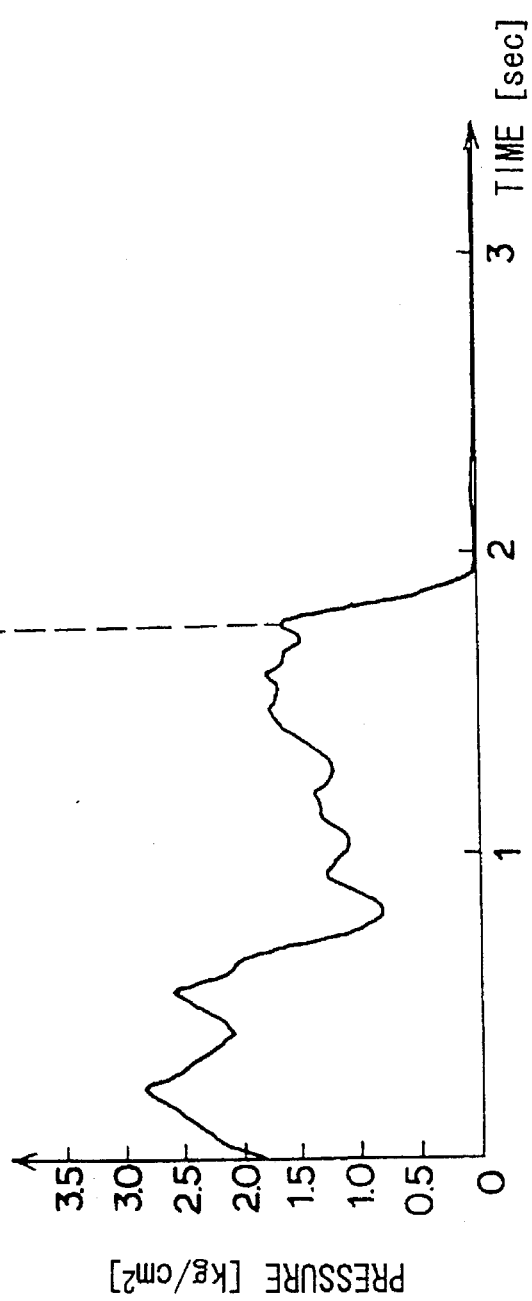
Figure 10A:
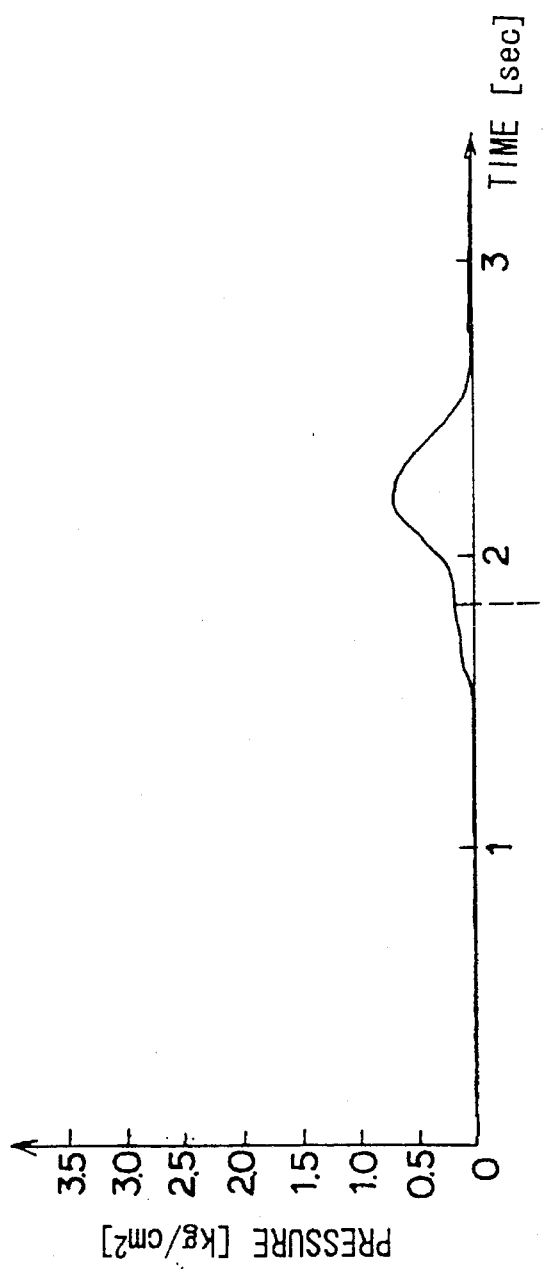
FIGS. 10A and 10B are characteristic curvilinear diagrams showing outputs obtained in a state where a telephone card is placed, i.e., in a negative O-ring state, as an embodiment of the body-compatibility judgment method.
Figure 10B:
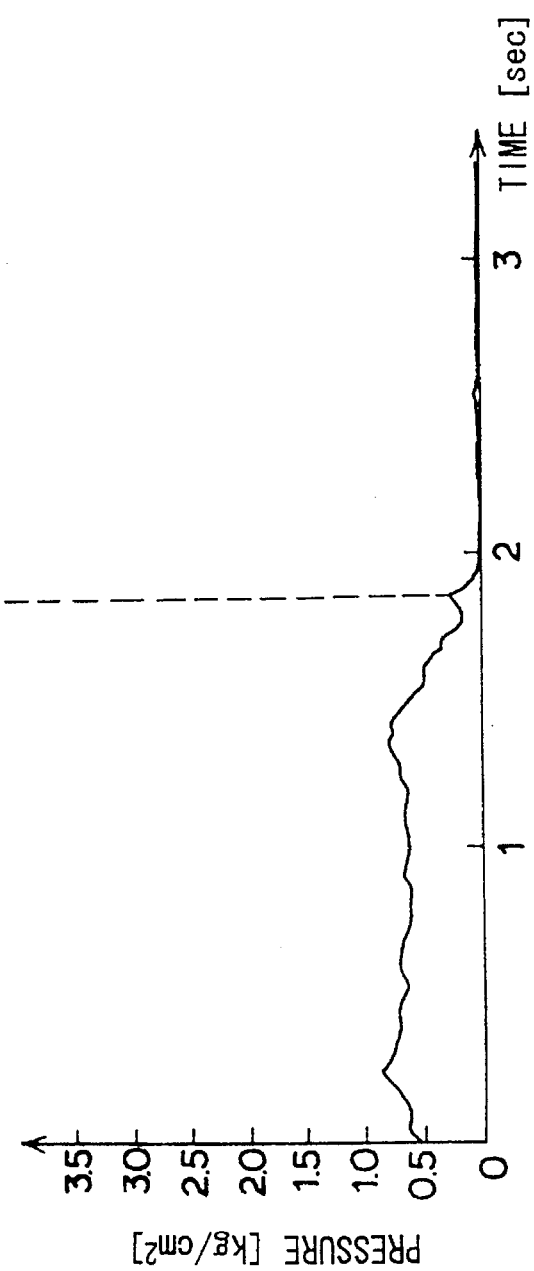
Figure 12A:
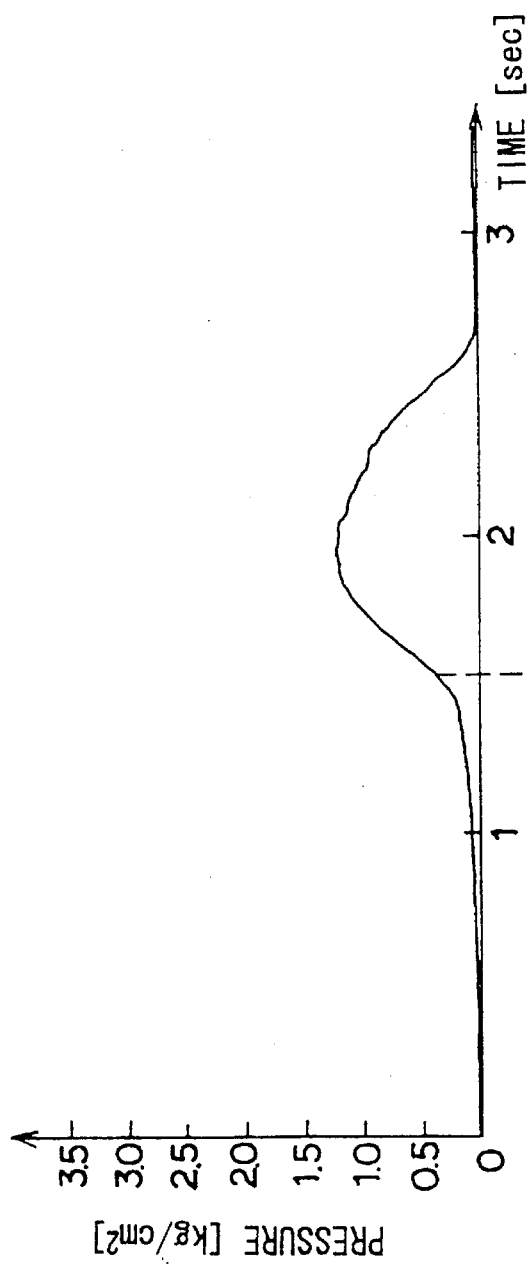
FIGS. 12A and 12B are characteristic curvilinear diagrams showing outputs obtained in a state where a card on which an arrow directed toward a fingertip is marked is placed, i.e., in a positive O-ring state, as an embodiment of the body-compatibility judgment method.
Figure 12B:
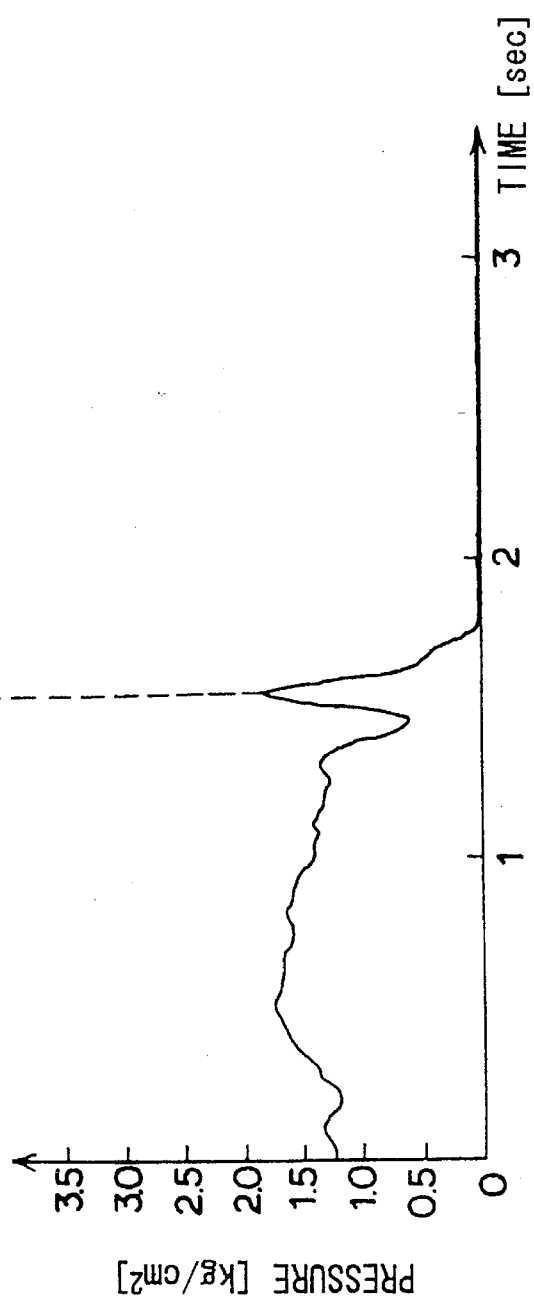
Figure 13A:
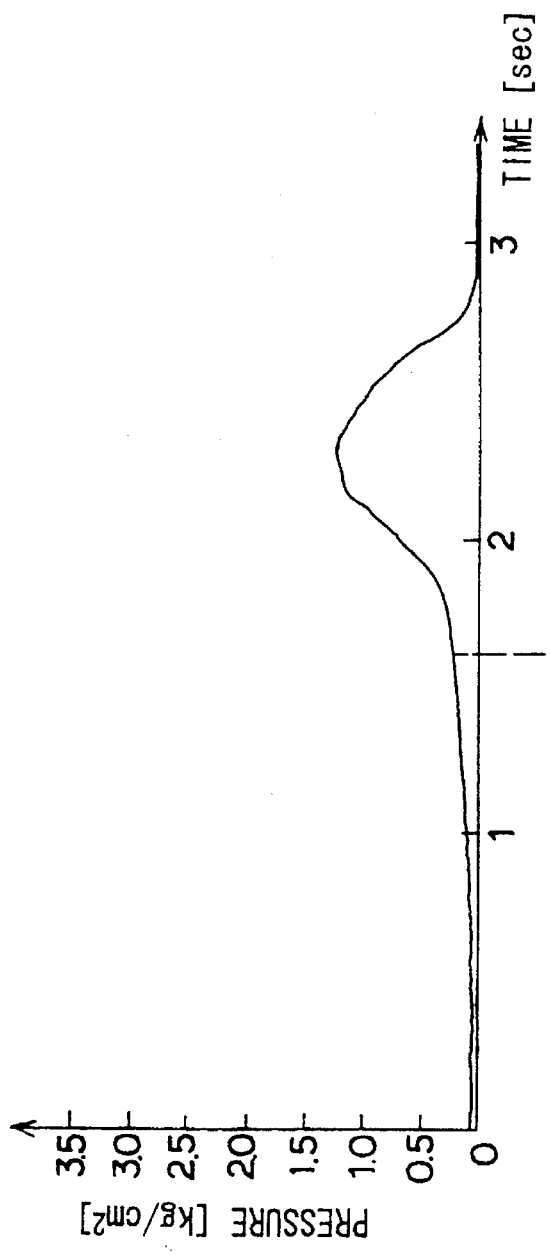
FIGS. 13A and 13B are characteristic curvilinear diagrams showing outputs obtained in a state where ginseng is placed, i.e., in a positive O-ring state, as an experimental example of the body-compatibility judgment method.
Figure 13B:
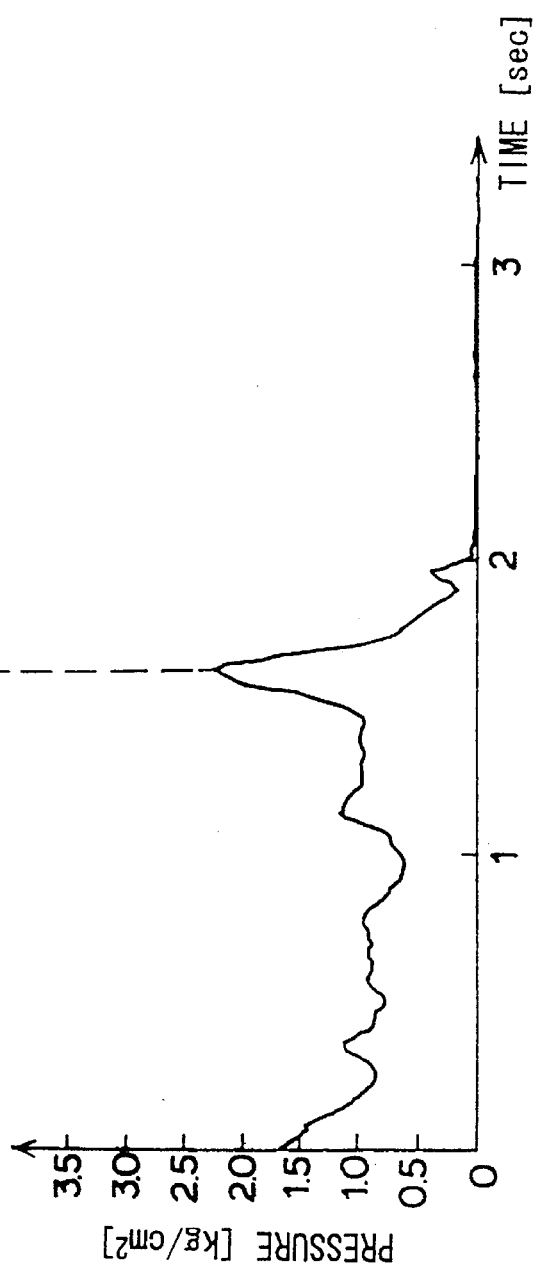

Hence, as an experimental example of this body-compatibility judgment method, FIGS. 9A and 9B shows the outputs obtained in a state of normal time, i.e, in the controlled state. In contrast, FIGS. 10A and 10B show the outputs obtained in a state where the telephone card is placed, i.e., in the negative O-ring state, and FIGS. 11A and 11B show the outputs obtained in a state where the card on which an arrow directed toward the inside of the human body is marked is placed, i.e., in the negative O-ring state. The telephone card and the arrow marked card are both incompatible with the human body. Also, FIGS. 12A and 12B show the outputs obtained in a state where the card on which an arrow directed toward a fingertip is marked is placed, i.e., in the positive O-ring state, and further, FIGS. 13A and 13B show the outputs obtained in a state where ginseng is placed, i.e., in the positive O-ring state, both of which show that the card on which an arrow directed toward a fingertip is marked and ginseng are compatible with the human body.

While, in this experimental example, the O-ring shape 6 of the fingertips of the subject is pulled apart in both the controlled state and in the positive O-ring state. The pressure value exerted when the fingertips of the O-ring shape 6 are pulled apart is 150 to 250 g/cm² in the controlled state, and 100 to 250 g/cm² in the negative O-ring state in which the telephone card is placed. Also, the pressure value is 100 g/cm² in the negative O-ring state in which the card on which an arrow directed toward the inside of the human body is placed, 300 g/cm³ in the positive O-ring state in which the card on which an arrow directed toward a fingertip is placed, and 200 g/cm² in the positive O-ring state in which ginseng is placed.

If it is assumed here that the pressure value in the controlled state is set to 200 g/cm², a pressure value larger than 200 g/cm² is the positive O-ring state, and a pressure value smaller than 200 g/cm² is the negative O-ring state, the pressure value becomes consistent with the result of the O-ring test. Therefore, if the pressure in the controlled state can be obtained appropriately, it is found that the pressure exerted when the fingertips of the O-ring test are pulled apart becomes consistent with the result of the O-ring test.

According to the structure described above, with of the voluntary-muscle strength measurement apparatus 1, the muscle strength as the fingertips of the O-ring shape 6 of the hand of the subject is pulled apart in the normal time is measured, and also the muscle strength as the O-ring shape 6 of the hand of the subject is pulled apart in a state in which a particular object is indicated is measured. The measured muscle strengths are compared to judge the compatibility of the particular object with the subject. Accordingly, there can be provided the body-compatibility judgment method which makes it possible to conduct the O-ring test accurately and objectively and make it possible to judge the compatibility with the human body with high reliability.

Figure 14:
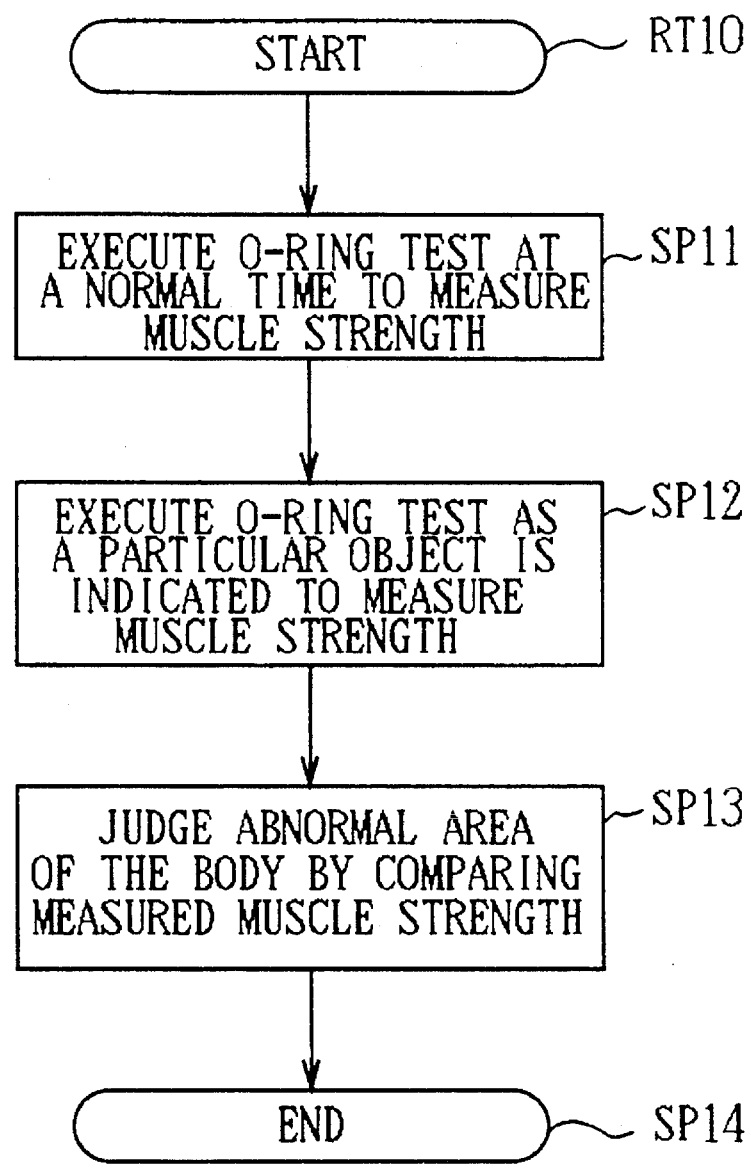
FIG. 14 is a flowchart showing an abnormal area judgment procedure according to an embodiment of the abnormal area judgment method of the present invention.

(1-3) Abnormal area judgment method by the voluntary-muscle strength measurement apparatus An abnormal area judgment method for judging an abnormal area of the body of a subject will hereinafter be described with the voluntary-muscle strength measurement apparatus 1 which is described above. In this embodiment, the subject indicates his or her internal organ from the outside with a wooden indication rod to judge whether or not the indicated organ is abnormal. This abnormal area judgment method is executed with an abnormal area judgment procedure RT10 shown in FIG. 14.

Figure 15A:
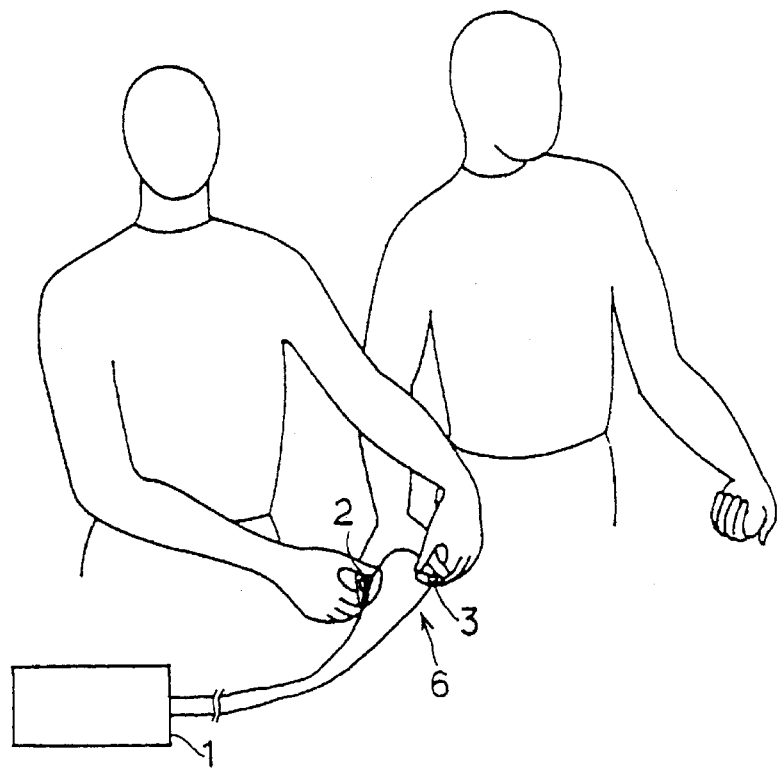
FIGS. 15A and 15B are schematic diagrams explaining the abnormal area judgment method in FIG. 14.

More specifically in this abnormal area judgment method, at step SP11, the O-ring test is executed at a normal time and the muscle strength at that time is measured with the voluntary-muscle strength measurement apparatus 1. As shown in FIG. 15A, it is assumed that the normal time is a state where nothing is placed on the subject's left hand, and the muscle strengths obtained at that time with the pressure sensors 2 and 3 are measured in utilizing the voluntary-muscle strength measurement apparatus 1. As described with reference to FIG. 2, for the O-ring shape 6 formed with the subject's right hand, one pressure sensor 2 attached to surgical tape 7 is placed in the vicinity of the second joint of the finger, and the other pressure sensor 3 is placed and held between the thumb and the finger.

Figure 15B:
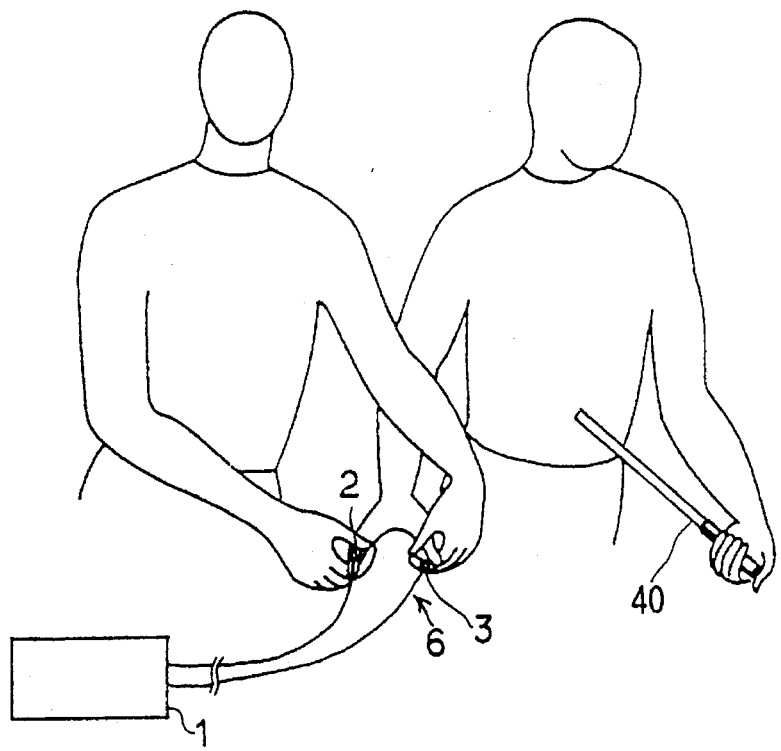

Next, at step SP12, the O-ring test is executed in a state where a predetermined organ of the body is indicated. As shown in FIG. 15B, the subject has a wooden indication rod 40 in his or her left hand and indicates the organ of the body. In this state, the O-ring test is executed, and the muscle strengths obtained with the pressure sensors 2 and 3 are measured in utilizing the voluntary-muscle strength measurement apparatus 1. At step SP13, the muscle strengths measured in the above steps SP11 and SP12 are compared to judge if the indicated organ is abnormal by whether it is the negative O-ring state, the controlled state, or the positive O-ring state.

According to the structure described above, with the voluntary-muscle strength measurement apparatus 1, the muscle strength as the fingertips of the O-ring shape 6 of the hand of the subject are pulled apart in the normal state is measured and also the muscle strength as the O-ring shape 6 of the hand of the subject is pulled apart in the state where a predetermined part of the body is indicated is measured. The measured muscle strengths are compared to judge if the predetermined part of the body is abnormal, so that there can be provided the abnormal area judgment method which makes it possible to conduct the O-ring test accurately and objectively and makes it possible to judge an abnormal area of the body with high reliability.

Figure 16:
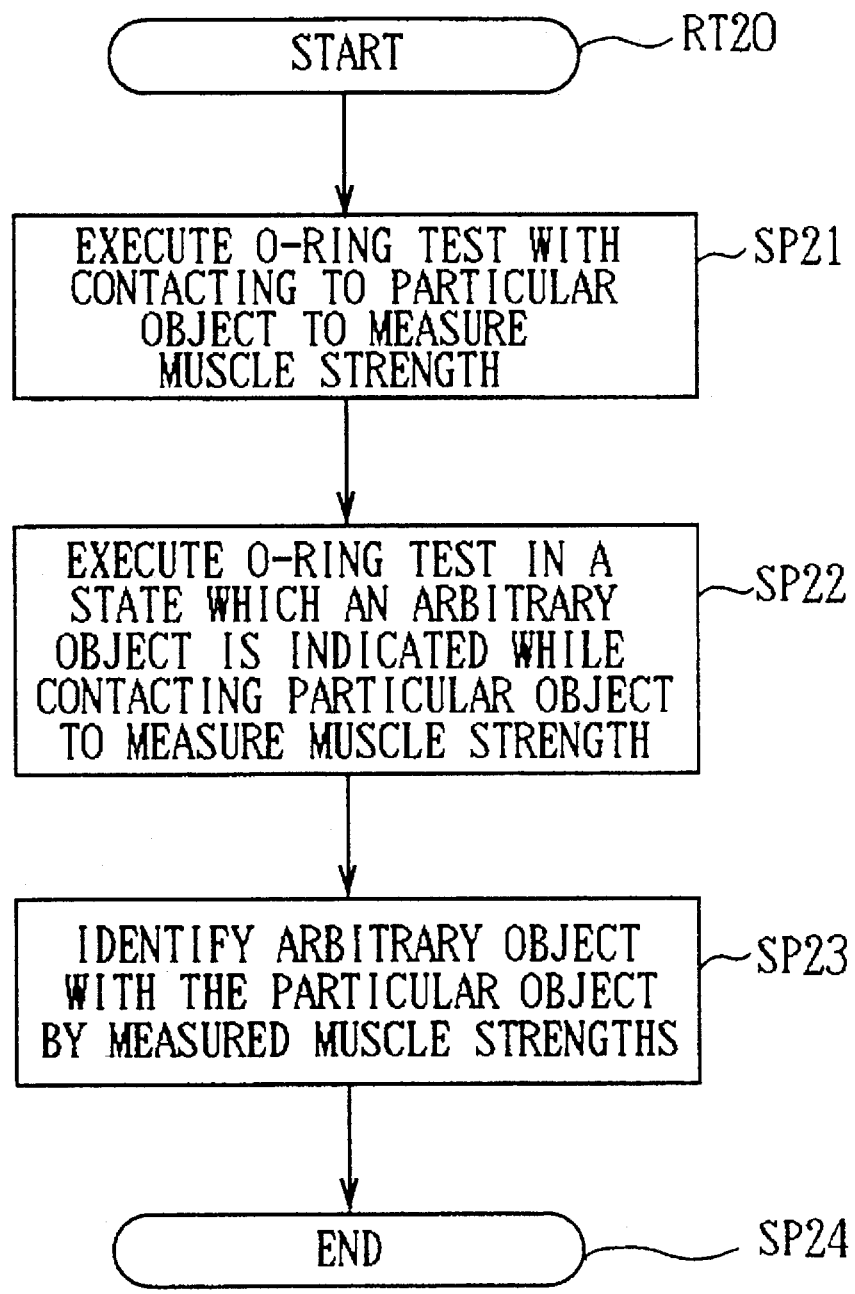
FIG. 16 is a flowchart showing the information identification procedure according to an embodiment of the information identification method of the present invention.

(1-4) Information identification method by the voluntary-muscle strength measurement apparatus A information identification method which judges whether an arbitrary object and a particular object have the same information will hereinafter be described with the voluntary-muscle strength measurement apparatus 1 which is described above. In this embodiment, the subject indicates an arbitrary object with a wooden indication rod and is able to judge if the arbitrary object has the same information as that of the particular object held by himself or herself. This information identification method is executed with an information identifying procedure RT20 shown in FIG. 16.

Figure 17A:
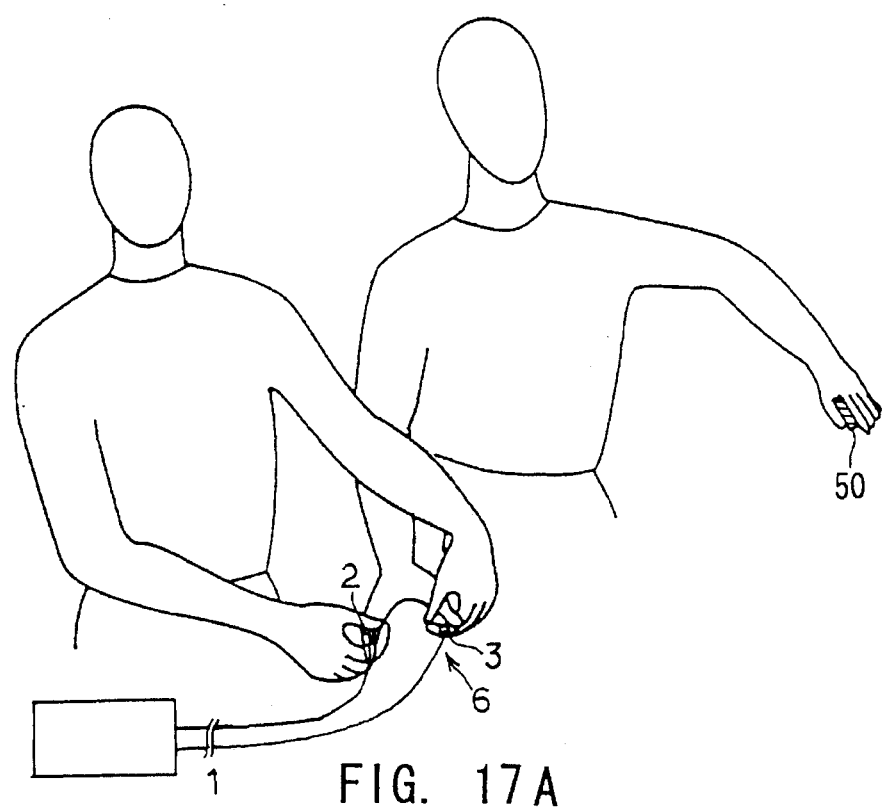
FIGS. 17A and 17B are schematic diagrams explaining the information identification method in FIG. 16.

More particularly, in this information identification method, at step SP21, the O-ring test is executed in a state where the subject is contacted with a particular object, and the muscle strength at that time is measured with the voluntary-muscle strength measurement apparatus 1. As shown in FIG. 17A, it is assumed that the normal time is a state in which a particular object 50 is placed on the subject's left hand, and the muscle strengths obtained at that time with the pressure sensors 2 and 3 are measured in utilizing the voluntary-muscle strength measurement apparatus 1. As described with reference to FIG. 2, for the O-ring shape 6 formed with the subject's right hand, one pressure sensor 2 attached to surgical tape 7 is placed in the approximate vicinity of the second joint of the finger, and the other pressure sensor 3 is placed and held between the thumb and the finger.

Figure 17B:
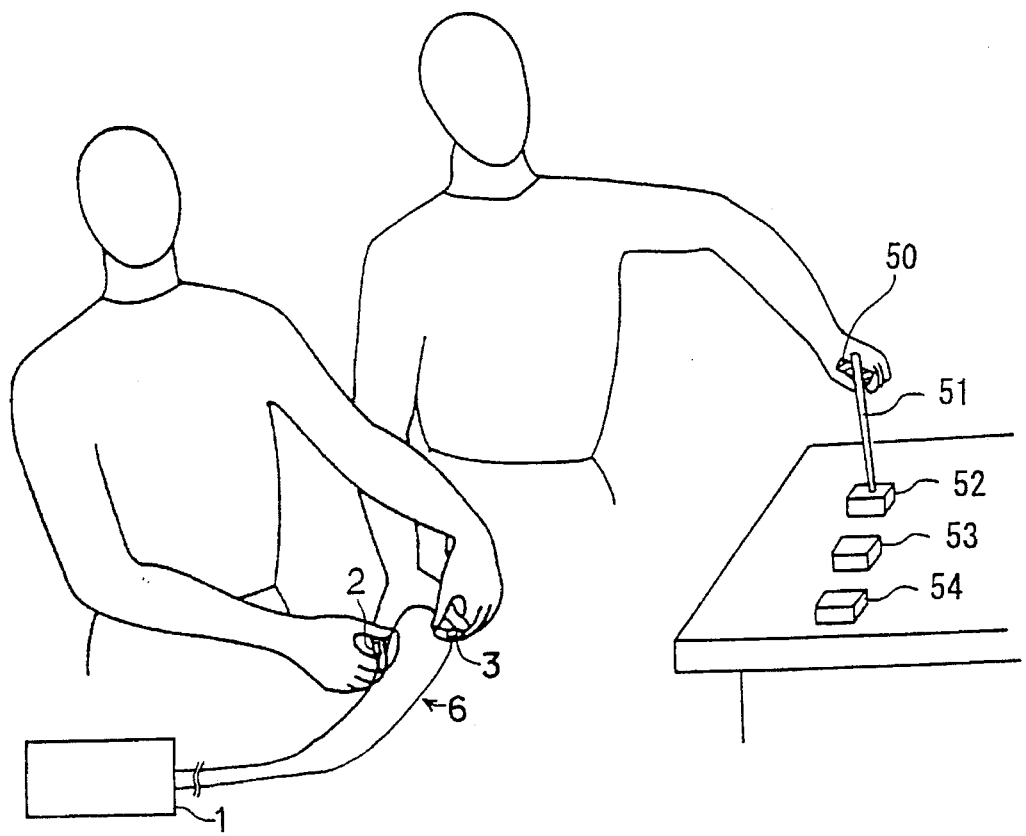

Next, at step SP22, the O-ring test is executed in a state where the particular object is contacted and an arbitrary object is indicated. As shown in FIG. 17B, the subject has the particular object 50 in his or her left hand and indicates an arbitrary object such as 52, 53, or 54 with the wooden indication rod 51. Each time the subject indicates an arbitrary object, the O-ring test is executed, and the muscle strengths obtained with the pressure sensors 2 and 3 are measured in utilizing the voluntary-muscle strength measurement apparatus 1. Furthermore, at step SP23, the muscle strengths measured in steps SP21 and SP22 are compared to judge if each of the indicated arbitrary object such as 52, 53, or 54 indicated with the wooden indication rod 51 has the same information as the particular object 50 by whether it is the negative O-ring state, the controlled state or the positive O-ring state.

According to the structure described above, with the voluntary-muscle strength measurement apparatus 1, the muscle strength is measured when the subject's left hand contacts the particular object 50 and the O-ring shape 6 of the hand of the subject is pulled apart. Also, when the subject's left hand contacts the particular object 50 and the arbitrary object 52, 53 or 54 is indicated and when the O-ring shape 6 of the hand of the subject is pulled apart, the muscle strength is measured. Then, the measured muscle strengths are compared to judge if the arbitrary objects 52, 53 and 54 and the particular object 50 have the same information. Accordingly, there can be provided the information identification method which makes it possible to conduct the O-ring test accurately and objectively and makes it possible to identify information with high reliability.

(1-5) Other embodiment

In the voluntary-muscle strength measurement apparatus described above, pressure sensors are placed on the fingertips of the O-ring and in the vicinity of the second joint of the finger. However, the position of pressure sensors are not only limited to this, but the same effect can be obtained as long as the muscle strength while the O-ring shape 6 is pulled apart can be detected and as long as it can be detected if the thumb and the finger forming the O-ring shape 6 are pulled apart. In addition, the shape of the pressure sensor itself is not only limited to a thin disc shape, but can take various types of shape.

Furthermore, in the voluntary-muscle strength measurement apparatus described above, the outputs of the pressure sensors are inputted to the pen recorder and, based on the graphs obtained resultingly, the muscle strength at the time when the fingertips of the O-ring shape are pulled apart is detected. However, the this invention is not only limited to this, but output of the pressure sensors may be taken into a computer as data and the like to process by statistical methods may be and used in the judgment of the O-ring test.

Figure 18A:
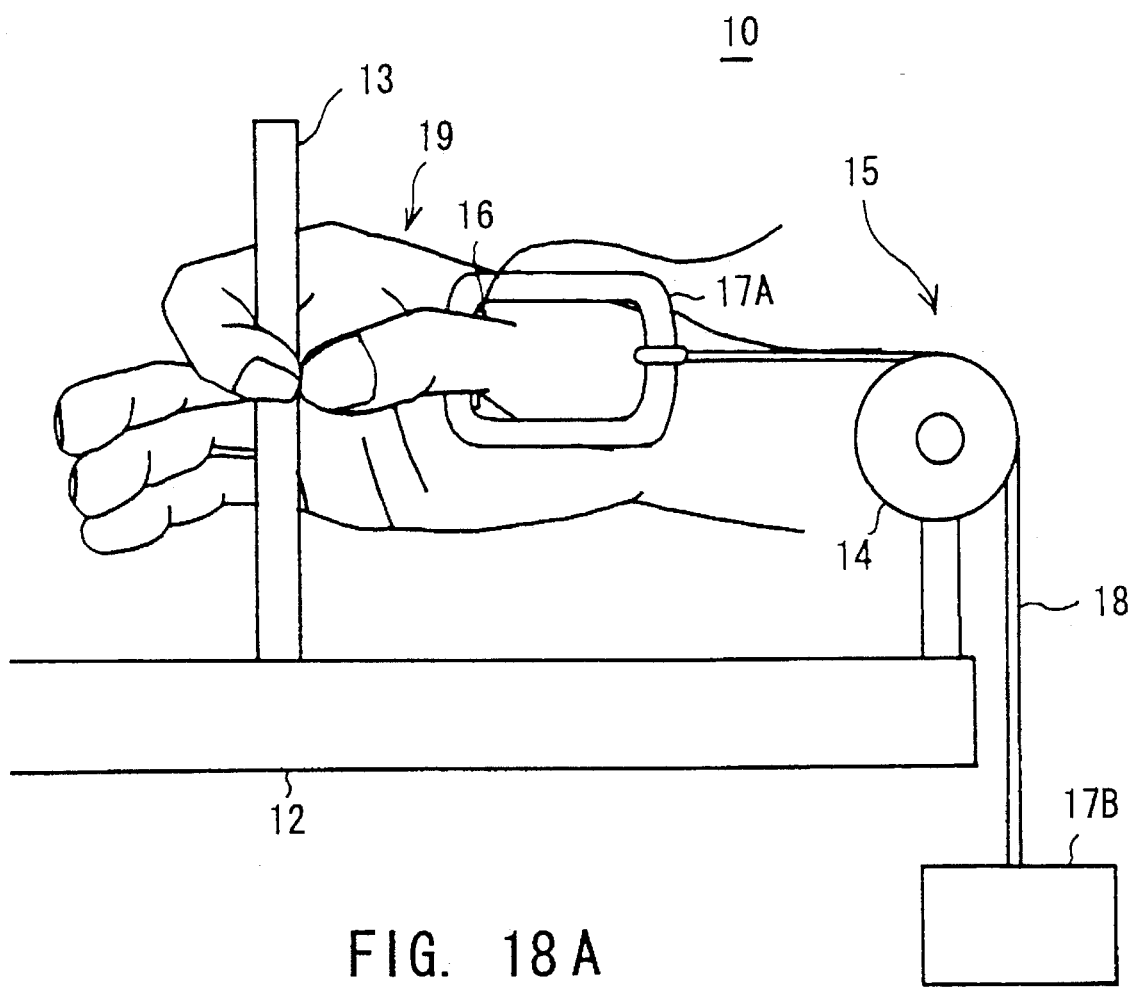
FIGS. 18A and 18B are schematic diagrams showing the construction of the muscular tonus state detection unit of a muscular tonus state judgment apparatus according to an embodiment of the present invention.
Figure 18B:
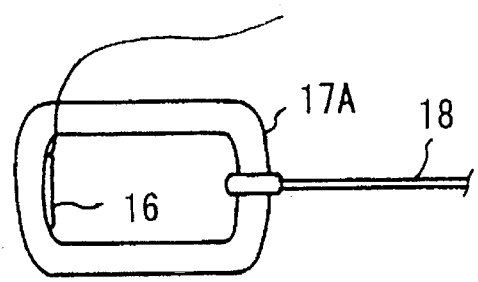

(2) Second Embodiments (2-1) Muscular tonus state measurement method of the embodiment In FIG. 18A, 10 denotes a muscular tonus state detection unit of a muscular tonus state judgment apparatus constructed in accordance with the present invention. The muscular tonus state detection unit 10 is composed of a vertical support bar 13 standing on a table 12, a pulley 14 at one end of the table 12, and a load application unit 15 using the pulley 14. The load application unit 15 consists of a ring 17A (FIG. 18B) having a pressure sensor 16 on the inner surface thereof, a weight 17B, and a wire 18 by which the ring 17A and the weight 17B are connected to each other. The load to be applied by the load application unit 15 is adjustable by changing the weight 17B.

In the muscular tonus state detector 10, the subject initially inserts the thumb of an O-ring shape 19 formed with the thumb and index finger, and then hangs the index finger on the vertical support bar 13. With this arrangement, when the subject puts force into the O-ring shape 19, a pressure corresponding to the load of the weight 17B can be applied from the outside. In this embodiment, it is measured how many seconds a state more than this pressure can continue, and thereby the muscular tonus state is judged to obtain the result of the O-ring test.

Figure 19:
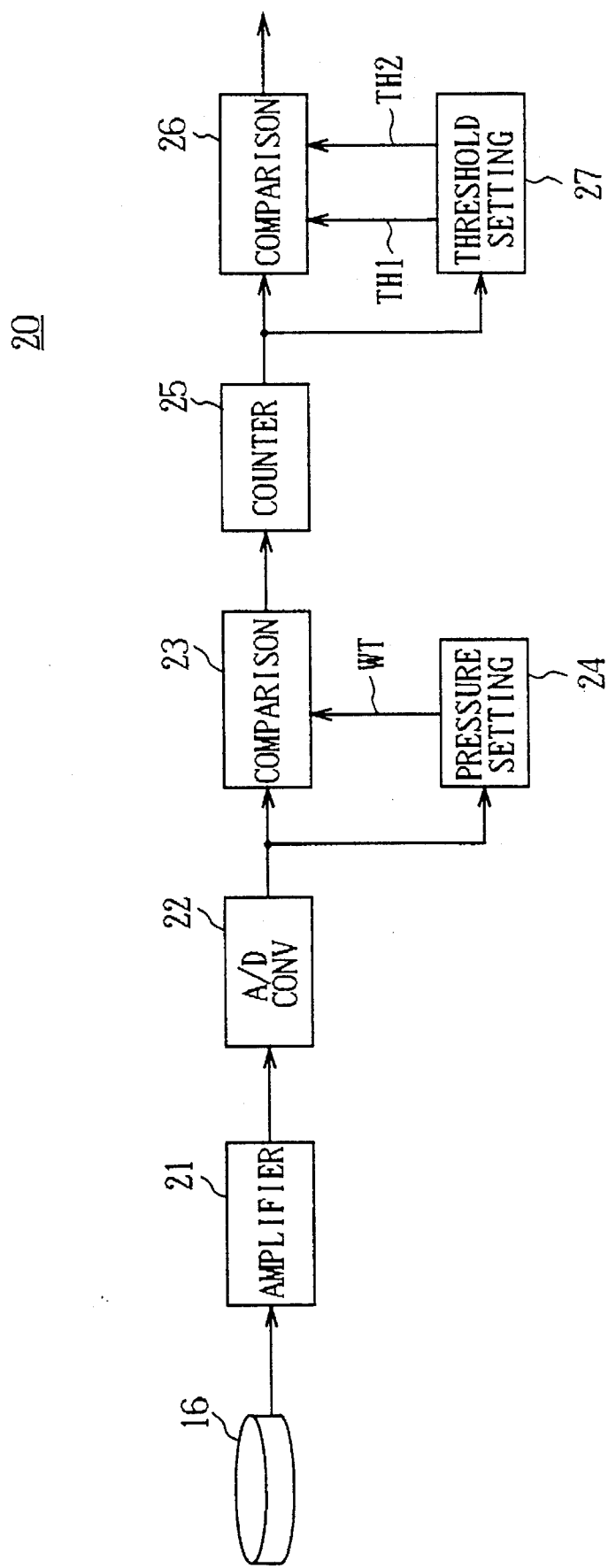
FIG. 19 is a block diagram showing the muscular tonus state judgment apparatus to which the muscular tonus state detection unit is connected.

The detection result of the pressure sensor 16 in the muscular tonus state detector 10 is inputted to the muscular tonus state judgment apparatus 20 shown in FIG. 19. In the muscular tonus state judgment apparatus 20, the detection result of the pressure sensor 16 is amplified at an amplifier 21, converted to the pressure value data at an analog-to-digital conversion circuit 22, and then inputted to a first comparison circuit 23 and a pressure value setting circuit 24. The pressure value setting circuit 24 sets a predetermined pressure value WT corresponding to the pressure value data gathered in the initial value setting process, and outputs it to the first comparison circuit 23. The first comparison circuit 23 compares the pressure value data to be inputted in the muscular tonus state detection process with the predetermined pressure value WT, and transmits the comparison result to a counter 25. Therefore, the counter 25 measures the period of time that the pressure value data is more than the predetermined pressure value. This time data is transmitted to a second comparison circuit 26 and a threshold value setting circuit 27.

The threshold value setting circuit 27 sets a first threshold value TH1 and a second threshold value TH2 corresponding to the time data gathered in the initial value setting process to output to the second comparison circuit 26. The second comparison circuit 26 compares the time data to be inputted in the muscular tonus state detection process with the first and second threshold values TH1 and TH2, and outputs a judgment result of the muscular tonus state based on the comparison result. The first threshold value TH1 is here set to a value greater than the second threshold value TH2, so that, if the time data is less than the second threshold value TH2, it is judged that the muscular tonus is a negative O-ring state; if the time data is more than the second threshold value TH2 and less than the first threshold value TH1, the muscular tonus is judged to be a controlled state; and if the time data is more than the first threshold value TH1, it is judged that the muscular tonus is a positive O-ring state.

In this O-ring test, the compatibility of the human body, an abnormal area, an information identification, and the like are judged by the muscular tonus state of the O-ring shape of the hand of the subject as the test result. It is to be noted here that the state of this O-ring shape is divided into a state where the O-ring shape cannot be pulled apart and a state where the O-ring shape is pulled apart. The state where the O-ring shape is pulled apart is hereinafter referred to as the negative O-ring state and, in the figures, that state is denoted by O(−). Furthermore, the state where the O-ring shape cannot be pulled apart is divided into a state where the O-ring shape is closed with a stronger force than usual, hereinafter referred to as "the positive O-ring state" and denoted by O(+) in the figures, and a state where the O-ring shape is closed with a force equal to a force at a normal time, hereinafter referred to as "the controlled state" and denoted by O(O) in the figures. The muscular tonus state is measured notably in the negative O-ring state. For example, in the case that the muscular tonus state indicates an abnormal area of the human body, the O-ring shape is pulled apart easily. However, if a peak detection value (maximum value) is obtained with a normal muscle-strength measurement machine, some cases arise in which the peak detection value is nearly the same value and a force is applied again in the pulling process.

Figure 20:
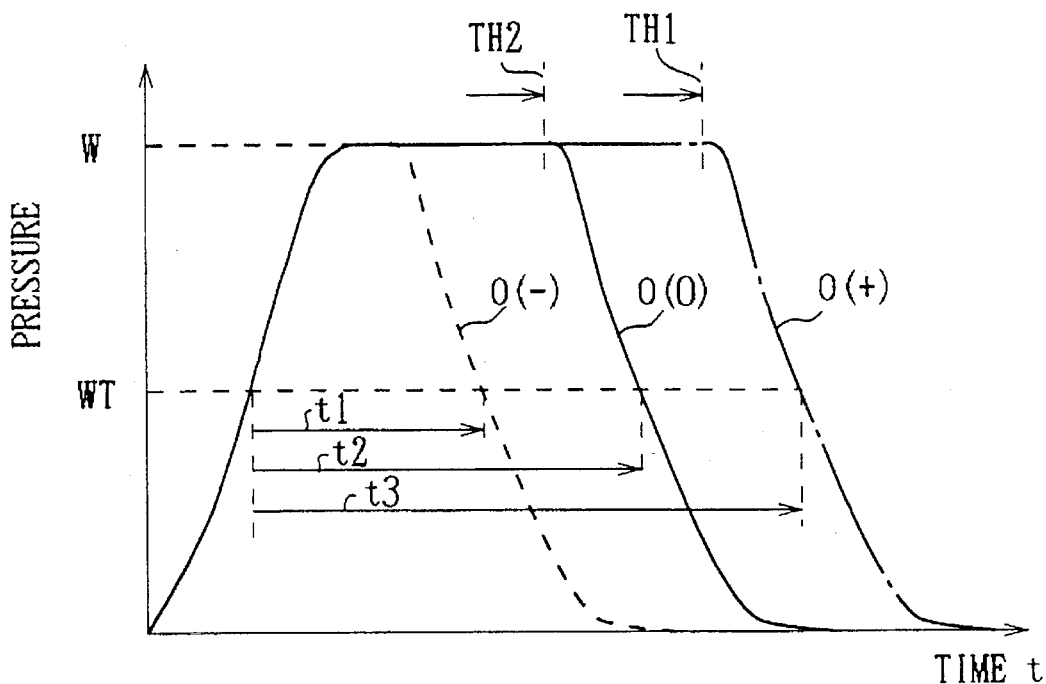
FIG. 20 is a characteristic curvilinear diagram explaining the method for judging the muscular tonus state.

In consideration of the above arrangement, the pressure W applied in advance as a competition of forces with the load application unit 15 is set as shown in FIG. 20. A value less than the pressure W, e.g., about ½ to ⅔ of the pressure W is set as the predetermined pressure value WT, and a period that the strength is more than the predetermined pressure value WT is held is set as an index. Therefore, the state of exhausting the muscle strength of the finger is accurately used to judge the muscular tonus state more reliably. More particularly, as shown in FIG. 20, periods of time t1, t2, and t3 that the pressure value data becomes more than the predetermined pressure value WT and then becomes less than the predetermined pressure value WT are identified, so that this muscular tonus state is judged.

Figure 21:
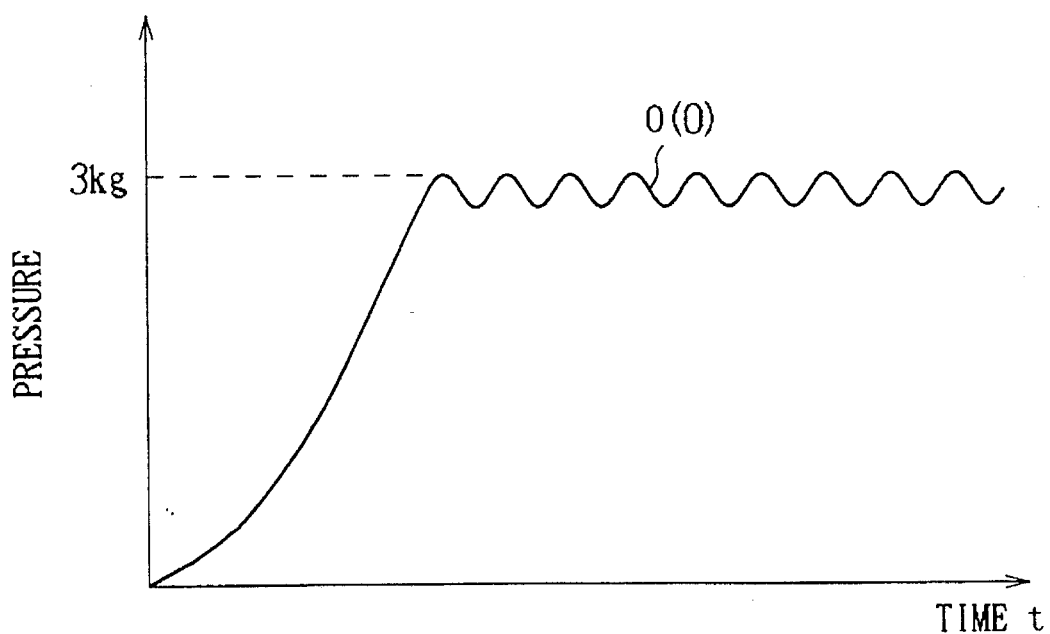
FIG. 21 is a characteristic curvilinear diagram explaining the measurement of a competitive force as an initial value setting process.

As the parameters, the pressure W to be applied at the load application unit 15, the predetermined pressure value WT, and the first and the second threshold values TH1 and TH2 are set, so that the time t1, t2, and t3 are judged. The respective values W, WT, TH1, and TH2 of these parameters are interlocked with one another, and further depend on the subject. The initial value setting process is therefore performed so that the measurement result can be obtained objectively and accurately. As this initial value setting process, as shown in FIG. 21, a pressure value W with which the O-ring shape competes is detected at a state where the subject is in a normal time, i.e., in the controlled state. In this figure, the muscular strength of the finger competes against 3 kg, and the finger is trembling to hold this competitive force.

Assuming that it is detected that the pressure W against which the O-ring shape competes is, for example, 3 kg, various loads of 3 kg (FIG. 22A), 4 kg (FIG. 22B), 3.5 kg (FIG. 22C) and 2.5 kg (FIG. 22D) are applied as the pressure value W to be applied from the outside onto the O-ring shape, and then the Oring test is performed so that the negative O-ring state, the controlled state, and the positive O-ring state are obtained. In this case, if 4 kg is applied as a load and the predetermined pressure value WT is set to about 2 kg, values of 0.6 sec, 1.2 sec, and 3.8 sec are obtained as the periods of time t1, t2, and t3. If the first and the second threshold values TH1 and TH2 are set based on the values obtained as the periods of time t1, t2, and t3, it is found that the muscular tonus state can be judged effectively based on the result of the O-ring test, as compared with the comparison of peak values.

According to the structure described above, the pressure W is applied from the outside through the pressure sensor 16 onto the O-ring shape 19 formed by the hand of the subject with the load application unit 15, and the pressure applied to the O-ring shape 19 is measured from the output from the pressure sensor 16. The muscular tonus state where pressure W is applied to the O-ring shape 19 is then judged by periods of time TH1 and TH2 showing that the measurement result is more than the predetermined pressure value WT. Accordingly, there can be provided the muscular tonus state judgment method and apparatus thereof which make it possible to conduct the O-ring test accurately and objectively and make it possible to detect the muscular tonus state with high reliability.

(2-2) Body-compatibility judgment method by the muscular tonus state judgment apparatus A body-compatibility judgment method for judging the compatibility of a particular object to the subject will hereinafter be described with the muscular tonus state judgment apparatus 20 described above. In this embodiment, a telephone card, ginseng, a card on which an arrow directed toward a fingertip is marked, and a card on which an arrow directed toward the inside of the human body is marked are employed as particular objects, and it is judged if these particular objects are compatible with the subject or not.

Figure 23:
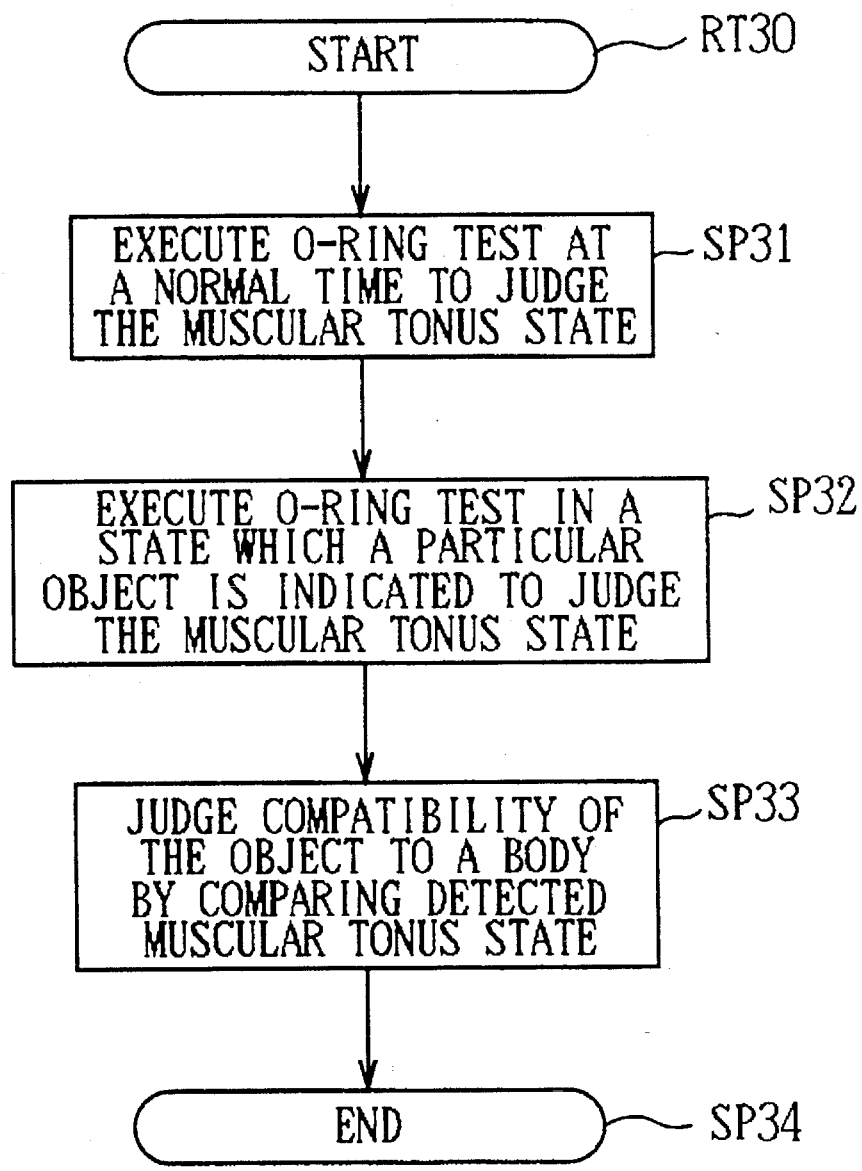
FIG. 23 is a flowchart showing a body compatibility judgment procedure according to an embodiment of the body-compatibility judgment method of the present invention.
Figure 24:
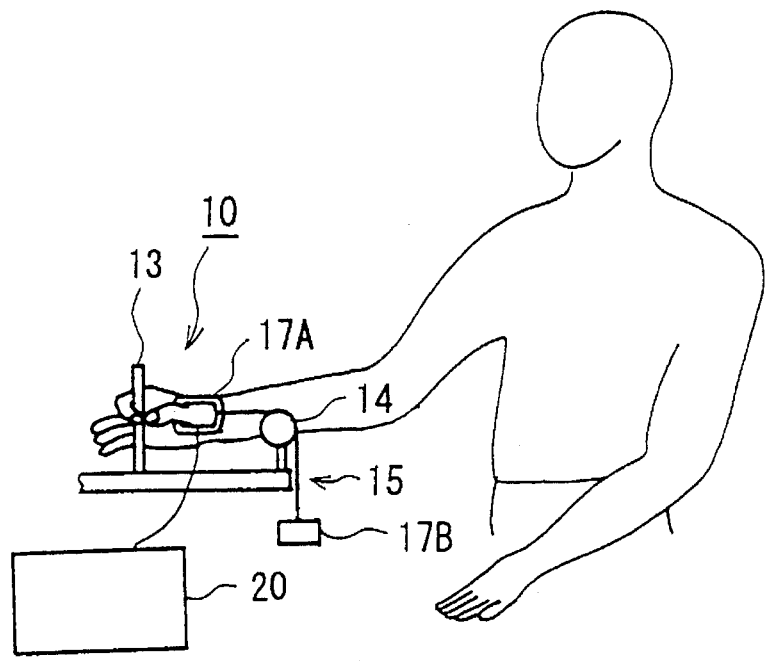
FIGS. 24A and 24B are schematic diagrams explaining the body-compatibility judgment method in FIG. 23.
Figure 24:
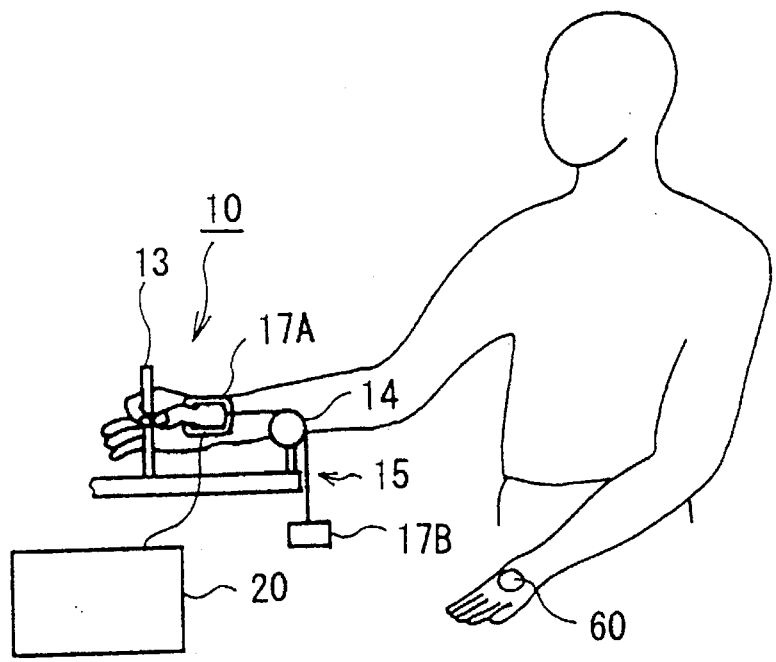

The body-compatibility judgment method is executed with a body-compatibility judging procedure RT30 such as that shown in FIG. 23. In step SP31, the O-ring test is executed at a normal time and the muscular tonus state at that time is measured with the muscular tonus state judging apparatus 20. As shown in FIG. 24A, the normal time is assumed as a state where nothing is placed on the subject's left hand, and the muscular tonus state is measured with the muscular tonus state judgment apparatus 20.

Next, in step SP32, the O-ring test is executed in a state where a particular object is indicated. As shown in FIG. 24B, the particular object 60, such as a telephone card, ginseng, a card on which an arrow directed toward a fingertip is marked, and a card on which an arrow directed toward the inside of the human body is marked, is placed on the subject's left hand, and the muscular tonus state is obtained with the muscular tonus state judging apparatus 20. In step SP33, the muscular tonus states measured in steps SP31 and SP32 are compared to judge if the particular object 60 is compatible with the subject.

Figure 22:
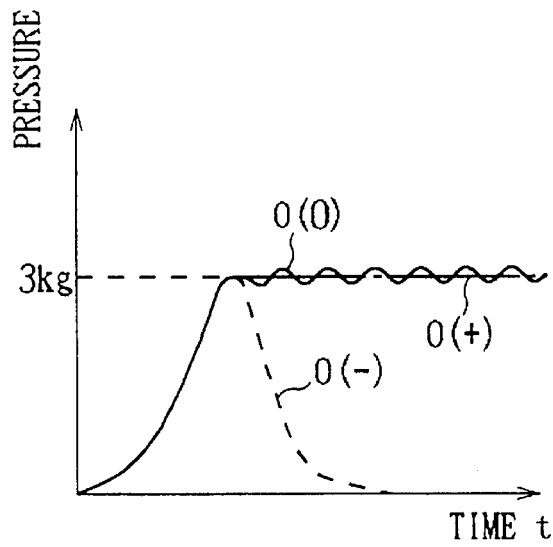
FIGS. 22A to 22D are characteristic curvilinear diagrams explaining the method of determination of a load to be set to the load application unit.
Figure 22:
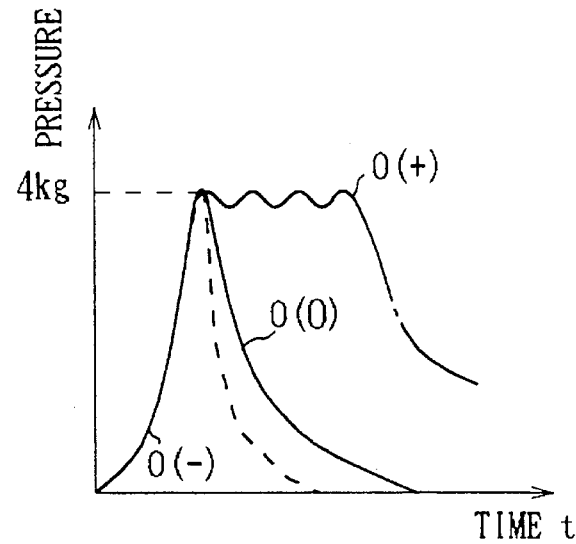
Figure 22:
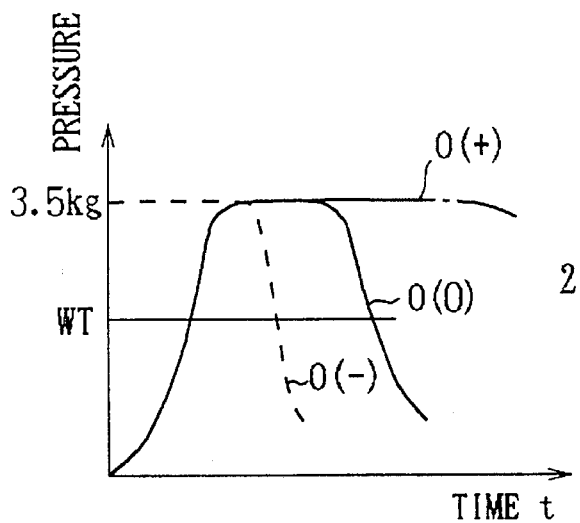
Figure 22:
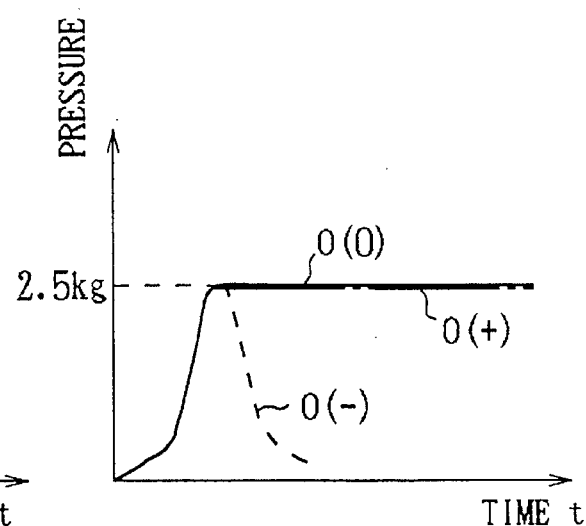

Hence, as an experimental example of this bodycompability judgment method, the muscular tonus state become the controlled state O(O) in the case of a normal time, as shown in FIG. 22C. When the telephone card or the card on which an arrow directed toward the inside of the human body is marked is placed on the subject's hand, the muscular tonus state becomes the O-ring negative state O(−). Therefore, in either case, neither the telephone card nor the arrow marked card are compatible with the human body. Also, when the card on which an arrow directed toward a fingertip is marked or ginseng is placed on the subject's hand, the muscular tonus state becomes the positive O-ring state O(+), so that these cases are compatible with the human body.

It is to be noted that, in the case where the initial value of the muscular tonus state judgment apparatus 10 is set optimally, when the period of time, that the pressure value indicated by the pressure sensor 16 is more than the predetermined pressure value WT, is more than the first threshold value TH2, the muscular tonus state can be judged to be the positive O-ring state O(+) where the particular object 60 is compatible with the subject. Also, when the period of time is less than the second threshold value TH1, the muscular tonus state can be judged to be the negative O-ring rate O(−) where the particular object 60 is not compatible with the subject.

According to the structure described above, with the muscular tonus state judgment apparatus 20, the pressure W is applied from the outside through the pressure sensor 16 to the O-ring shape 19 formed with the thumb and one of the fingers of the hand of the subject and the subject contacts a particular object 60. Then the pressure W applied to the O-ring shape 19 is measured from the output of the pressure sensor 16, and, when the period of time, that the measurement result is more than the predetermined pressure value WT, is more than the first threshold TH2, it is judged that the particular object 60 is compatible with the subject. When the period of time that the measurement result is more than the predetermined pressure value WT and less than the second threshold TH1, it is judged that the particular object 60 is not compatible with the subject. Accordingly, there can be provided the bodycompatibility judgment method which makes it possible to conduct the O-ring test by judging the muscular tonus state accurately and objectively and also it possible to judge the compatibility with the human body with high reliability.

Figure 25:
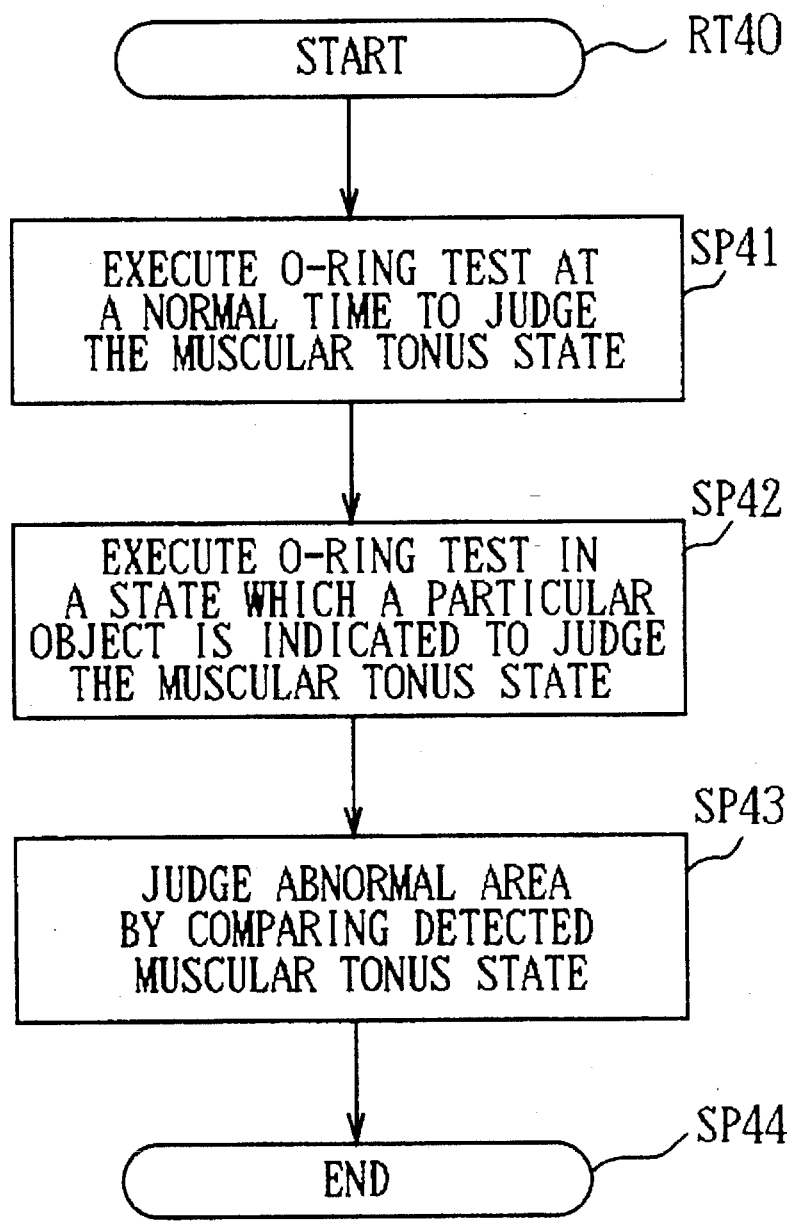
FIG. 25 is a flowchart showing an abnormal area judging procedure according to an embodiment of the abnormal area judgment method of the present invention.

(2-3) Abnormal area judgment method by the muscular tonus state judgment apparatus An abnormal area judgment method for judging an abnormal area of the body of a subject will hereinafter be described with the above-described muscular tonus state judgment apparatus 20. In this embodiment, the subject indicates his or her internal organ from the outside with a wooden indication rod, and judges if the indicated organ is abnormal. This abnormal area judgment method is executed with an abnormal area judgment procedure RT40 as shown in FIG. 25.

Figure 26:
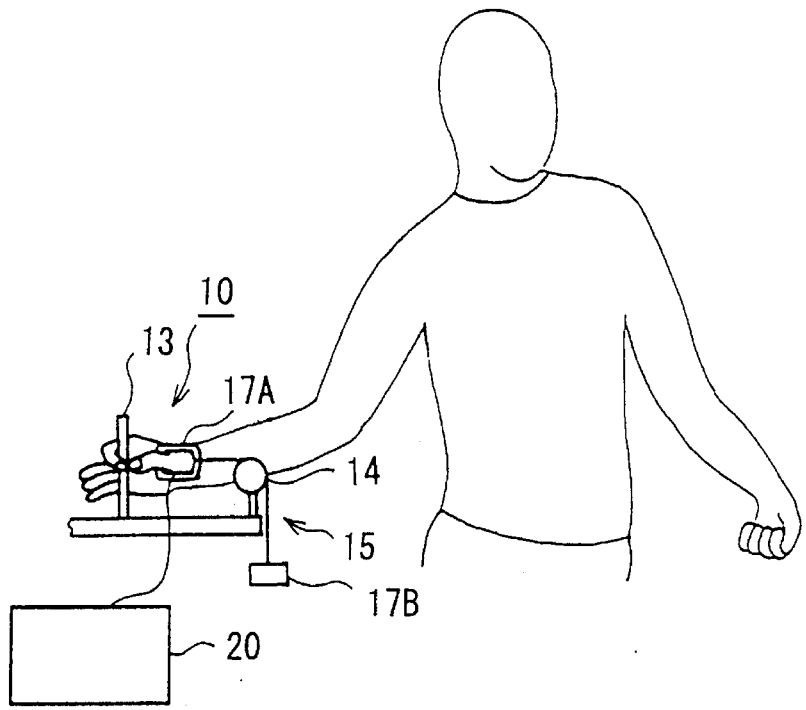
FIGS. 26A and 26B are schematic diagrams explaining the abnormal area judgment method in FIG. 25.
Figure 26:
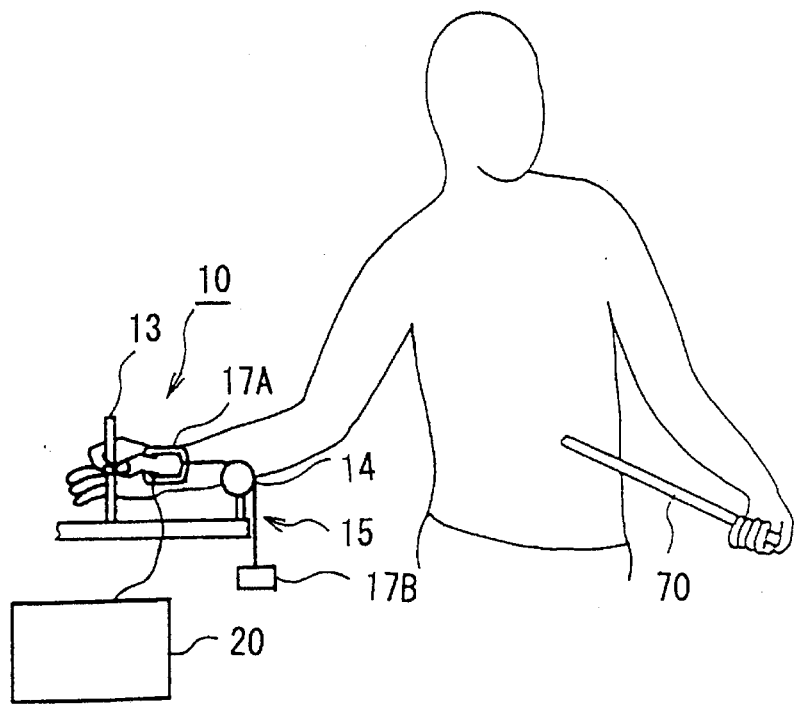

In the abnormal area judgment method, at step SP41, the O-ring test is executed at a normal time and the muscular tonus state at that time is measured with the muscular tonus state judgment apparatus 20. As shown in FIG. 26A, the normal time is assumed as a state where nothing is placed on the subject's left hand, and the muscular tonus state at that time is judged with the muscular tonus state judgment apparatus 20.

Next, at step SP42, the O-ring test is executed in a state where a predetermined organ of the body is indicated. As shown in FIG. 26B, the subject has a wooden indication rod 70 in his or her left hand and indicates the organ of the body. In this state, the O-ring test is executed, and the muscular tonus state at that time is judged with the muscular tonus state judgment apparatus 20. At step SP43, the muscular tonus states judged in the above-described steps SP41 and SP42 are compared to judge if the indicated organ is abnormal by whether the muscular tonus state is the negative O-ring state O(−), the controlled state, or the positive O-ring state O(+).

It is to be noted that, in the case where the initial value of the muscular tonus state judgment apparatus 20 is set optimally, when the period of time, that the pressure value data indicated by the pressure sensor 16 is more than the predetermined pressure value WT, is less than the second threshold value TH1, it can be judged that the muscular tonus state is the negative O-ring state O(−) and the particular object is not compatible with the subject.

According to the structure described above, with the muscular tonus state judgment apparatus 20, the pressure W is applied from the outside through the pressure sensor 16 to the O-ring shape 19 formed with the thumb and one of the fingers of the hand of the subject. The subject indicates a predetermined part of the body and the pressure W applied to the O-ring shape 19 is measured from the output of the pressure sensor 16. When the period of time, that the measurement result is more than the predetermined pressure value WT, is less than the second threshold TH1, the predetermined part of the subject's body is judged to be abnormal. Accordingly, there can be provided the abnormal area judgment method which makes it possible to conduct the O-ring test by judging the muscular tonus state accurately and objectively and also makes it possible to judge an abnormal area of the body with high reliability.

Figure 27:
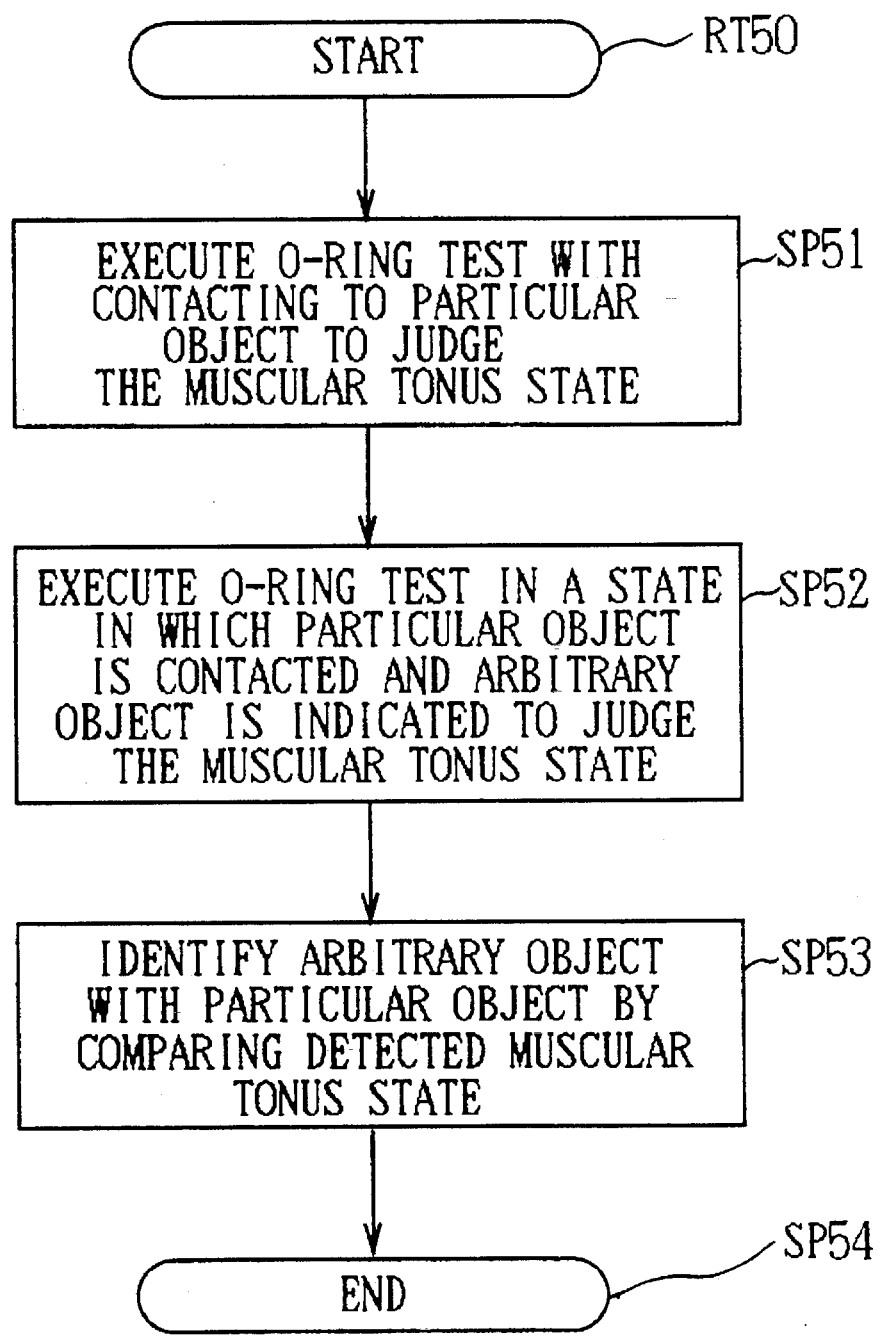
FIG. 27 is a flowchart showing an information identification procedure according to an embodiment of the information identification method of the present invention.

(2-4) Information identification method by the muscular tonus state judgment apparatus An information identification method which judges whether an arbitrary object and a particular object have the same information will hereinafter be described with the muscular tonus state judgment apparatus 20 described above. In this embodiment, the subject indicates an arbitrary object with a wooden indication rod and can judge if the arbitrary object has the same information as that of the particular object held by the subject. This information identification method is executed with an abnormal area judgment procedure RT50 as shown in FIG. 27.

Figure 28:
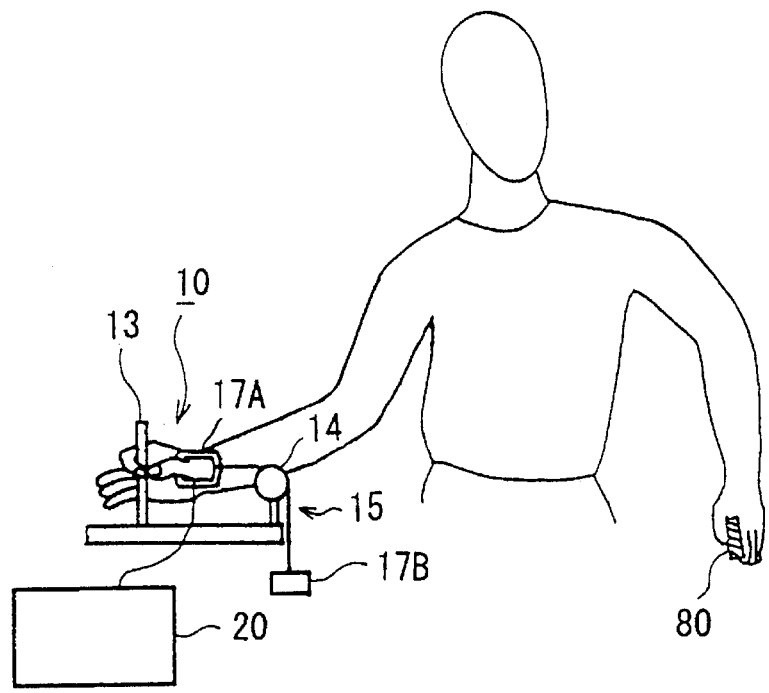
FIGS. 28A and 28B are schematic diagrams explaining the information identification method of FIG. 27.
Figure 28:
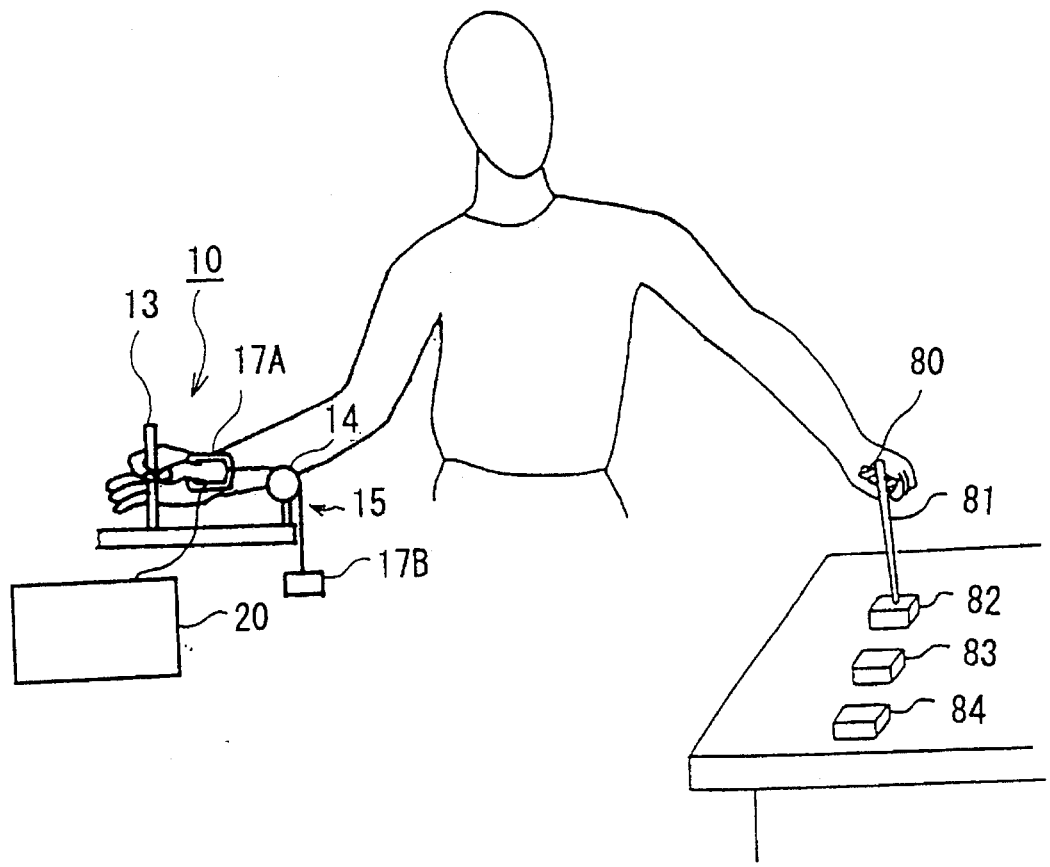

More particularly, in this information identification method, at step SP51, the O-ring test is executed in a state where the subject is contacted with a particular object, and the muscular tonus state at that time is measured with the muscular tonus state judgment apparatus 20. As shown in FIG. 28A, a normal time is assumed as a state where a particular object 80 is placed on the subject's left hand, and the muscular tonus state is obtained at that time with the muscular tonus state judgment apparatus 20.

Next, in step SP52, the O-ring test is executed in a state where the particular object is contacted and an arbitrary object is indicated. As shown in FIG. 28B, the subject has the particular object 80 in his or her left hand and indicates arbitrary objects such as objects 82 to 84 with the wooden indication rod 81. Each time the arbitrary object is indicated, the O-ring test is performed, and the muscular tonus state is measured with the muscular tonus state judgment apparatus 20. Furthermore, in step SP53, the muscular tonus states measured in steps SP51 and SP52 are compared to judge if each of the indicated arbitrary objects has the same information as the particular object 80 according to whether it is the negative O-ring state, the controlled state or the positive O-ring state.

It is noted that, in the case where the initial value of the muscular tonus state judgment apparatus 20 is set optimally, when the period of time, that the pressure value indicated by the pressure sensor 16 is more than the predetermined pressure value WT, is less than the second threshold value TH1, it can be judged that the muscular tonus state is the negative O-ring state O(−) where the particular object 80 and the arbitrary object 82, 83, or 84 have the same information.

According to the structure described above, with the muscular tonus state judgment apparatus 20, the pressure W is applied from the outside through the pressure sensor 16 to the O-ring shape 19 formed with the thumb and one of the fingers of the hand of the subject. The subject contacts a particular object 80 and an arbitrary object 82, 83 or 84 is indicated, and then the pressure W applied to the O-ring shape 19 is measured from the output of the pressure sensor 16. When the period of time, that the measurement result is more than the predetermined pressure value WT, is less than the second threshold TH1, the particular object 80 is judged to have the same information as the arbitrary object 82 to 84. Accordingly, there can be provided the information identification method which makes it possible to conduct the O-ring test by judging the muscular tonus state accurately and objectively and also makes it possible to identify information with high reliability.

(2-5) Other embodiments

With the embodiment of the muscular tonus state judgment apparatus of this invention described above, a substantially constant pressure is applied to the O-ring shape with the load application unit. However, this invention is not only limited to this, but the variable pressure can also be applied, such as increasing the pressure gradually, and so on. In addition, the pressure to be applied to the O-ring shape of the subject is not only limited to the load application unit, but a pressure may also be applied with the O-ring shapes formed by the hands of the examiner.

Furthermore, in the muscular tonus state judgment apparatus described above, the outputs of the muscular tonus state are obtained from the comparison circuit. However, this invention is not only limited to this, but the output may be outputted to a pen recorder, or taken into a computer as data to process by using statistical methods, which can be used for the judgment of the O-ring test.

While there has been described in connection with the preferred embodiments of the invention, it will be obvious to those skilled in the art that various changes and modifications may be aimed, therefore, to cover in the appended claims all such changes and modifications as fall within the true spirit and scope of the invention.

What is claimed is:

1. A voluntary-muscle strength measurement method for measuring muscle strength of a voluntary muscle as an O-ring shape formed with a thumb and one of the fingers of a hand of a subject is pulled apart, said method comprising the steps of:

placing a first sensor on at least one point on said thumb or said one of the fingers;

placing a second sensor between said thumb and said one of the fingers;

detecting with said first sensor said muscle strength as said O-ring shape of the hand of the subject is pulled apart;

detecting with said second sensor whether said thumb and said one of the fingers are pulled apart; and measuring said muscle strength at a time when said thumb and said one of the fingers are pulled apart based on outputs of said first and second sensors.

2. The method as set forth in claim 1, wherein said step of detecting said muscle strength with said first sensor comprises the step of pulling said O-ring shape apart with a force generated by an examiner.

3. The method as set forth in claim 1, further comprising the step of tracking said outputs of said first and second sensors over time.

4. A voluntary-muscle strength measurement apparatus for measuring muscle strength of a voluntary muscle as an O-ring shape formed with a thumb and one of the fingers of a hand of a subject are pulled apart, comprising:

a first sensor for detecting said muscle strength as said O-ring shape of the hand of the subject is pulled apart, said first sensor being placed on at least one point on said thumb or said one of the fingers;

a second sensor for detecting whether said thumb and said one of the fingers are pulled apart, said second sensor being placed between said thumb and said one of the fingers; and muscle strength measurement means for receiving outputs of said first and second sensors and for measuring said muscle strength at a time when said thumb and said one of the fingers are pulled apart based upon the outputs from said first and second sensors.

5. The apparatus as set forth in claim 4, wherein said O-ring shape of the hand of the subject is pulled apart by a force generated by an examiner.

6. The apparatus as set forth in claim 4, wherein said O-ring shape of the hand of the subject is pulled apart by a constant force.

7. The apparatus as set forth in claim 4, wherein said muscle strength measurement means comprises a pen recorder for tracking said outputs of said first and second sensors.

8. The apparatus as set forth in claim 4, wherein said first and second sensors each comprise a strain gauge.

* * * * *